US010214732B2

(12) United States Patent
Pillai et al.

(10) Patent No.: US 10,214,732 B2
(45) Date of Patent: Feb. 26, 2019

(54) LYSIN AGENT AND METHOD OF USE FOR DIAGNOSTIC TESTING

(71) Applicant: The United States of America, as represented by the Secretary of Homeland Security, Washington, DC (US)

(72) Inventors: Segaran Pillai, Laurel, MD (US); Linda Weigel, Decatur, GA (US); Bernard Quigley, Atlanta, GA (US); David R. Hodge, Washington, DC (US)

(73) Assignee: The United States of America, as represented by the Secretary of Homeland Security, Washington, DC (US)

( * ) Notice: Subject to any disclaimer, the term of this patent is extended or adjusted under 35 U.S.C. 154(b) by 20 days.

(21) Appl. No.: 15/047,319

(22) Filed: Feb. 18, 2016

(65) Prior Publication Data

US 2017/0240876 A1    Aug. 24, 2017

(51) Int. Cl.
| | | |
|---|---|---|
| *C12N 9/24* | (2006.01) | |
| *C12Q 1/689* | (2018.01) | |
| *A61K 38/47* | (2006.01) | |
| *A61K 38/12* | (2006.01) | |
| *A01N 47/44* | (2006.01) | |

(52) U.S. Cl.
CPC ........... *C12N 9/2405* (2013.01); *A01N 47/44* (2013.01); *A61K 38/12* (2013.01); *A61K 38/47* (2013.01); *C12Q 1/689* (2013.01); *C12Y 302/01* (2013.01)

(58) Field of Classification Search
None
See application file for complete search history.

(56) References Cited

U.S. PATENT DOCUMENTS

2004/0029129 A1* 2/2004 Wang ................... C07K 14/195
435/6.18

OTHER PUBLICATIONS

Protein Man—A Look Into the 6XHIS Tag and Its Uses Published by G-Biosciences, Oct. 20, 2014 Obtained at tps://info.gbiosciences.com/blog/bid/202308/alookintothe6xhistaganditsuses.*
Appendix A—Allingment of Wang Seq. ID No. 45469 with instant SEQ ID No. 2.*
Appendix B—Alignment of Wang SEQ ID No. 9285 with instant SEQ ID No. 1.*

Altschul, Stephen F., Warren Gish, Webb Miller, Eugene W. Myers, and David J. Lipman. "Basic Local Alignment Search Tool." Journal of Molecular Biology 215 (1990): 403-10. Print.
Borysowski, Jan, Beata Weber-Dabrowska, and Andrzej Gorski. "Bacteriophage Endolysins as a Novel Class of Antibacterial Agents." Experimental Biology and Medicine 231.4 (2006): 366-77. Print.
Candela, Thomas, Stavroula Balomenou, Willy Aucher, Vassilis Bouriotis, Jean-Pierre Simone, Agnes Fouet, and Ivo G. Boneca. "N-Acetylglucosamine Deacetylases Modulate the Anchoring of the Gamma-Glutamyl Capsule to the Cell Wall of Bacillus Anthracis." Microbial Drug Resistance 20.3 (2014): 222-30. Print.
Carrillo, Humberto, and David Lipman. "The Multiple Sequence Alignment Problem in Biology." Society for Industrial and Applied Mathematics Journal on Applied Mathematics 48.5 (1988): 1073-082. Print.
Devereux, John, Paul Haeberli, and Oliver Smithies. "A Comprehensive Set of Sequence Analysis Programs for the VAX." Nucleic Acids Research 12.1 (1984): 387-95. Print.
Dolz, Reinhard. "GCG: Comparison of Sequences." Ed. A. M. Griffin and H. G. Griffin. Methods in Molecular Biology, vol. 24 Computer Analysis of Sequence Data, Part I. Totowa: Humana, 1994. 65-82. Print.
Dolz, Reinhard. "GCG: Production of Multiple Sequence Alignment." Ed. A. M. Griffin and H. G. Griffin. Methods in Molecular Biology, vol. 24 Computer Analysis of Sequence Data, Part I. Totowa: Humana, 1994. 83-99. Print.
Henikoff, Steven, and Jorja G. Henikoff. "Amino Acid Substitution Matrices from Protein Blocks." Proceedings of the National Academy of Sciences USA 89 (1992): 10915-0919. Print.
Needleman, Saul B., and Christian D. Wunsch. "A General Method Applicable to the Search for Similarities in the Amino Acid Sequence of Two Proteins." Journal of Molecular Biology 48 (1970): 443-53. Print.
Pearson, William Ft, and David J. Lipman. "Improved Tools for Biological Sequence Comparison." Proceedings of the National Academy of Sciences 85 (1988): 2444-448. Print.
Schuch, Raymond, Daniel Nelson, and Vincent A. Fischetti. "A Bacteriolytic Agent That Detects and Kills Bacillus Anthracis." Nature 418 (2012): 884-89. Print.
Yoong, Pauline, Raymond Schuch, Daniel Nelson, and Vincent A. Fischetti. "PlyPH, a Bacteriolytic Enzyme with a Broad PH Range of Activity and Lytic Action against Bacillus Anthracis." Journal of Bacteriology 188.7 (2006):2711-714. Print.

* cited by examiner

*Primary Examiner* — Addison D Ault
(74) *Attorney, Agent, or Firm* — Lavanya Ratnam; Trenton Roche; Joseph Hsiao

(57) ABSTRACT

Disclosed herein are the identification, cloning, and optimizing the lytic activity of one or more novel *Bacillus* lysin proteins, a method of selecting a lysin agent for use in molecular diagnostic testing that includes analyzing genome databases for *Bacillus anthracis* and near neighbors, selecting candidate genes encoding potential lytic enzymes based on conserved amino acid motifs as determined in peptidoglycan hydrolases, cloning the candidate genes in expression vector, isolating proteins thereof, and testing for lytic activity against *Bacillus anthracis*, and selecting an optimum gene of the candidate genes for optimizing lysis conditions.

31 Claims, 9 Drawing Sheets
Specification includes a Sequence Listing.

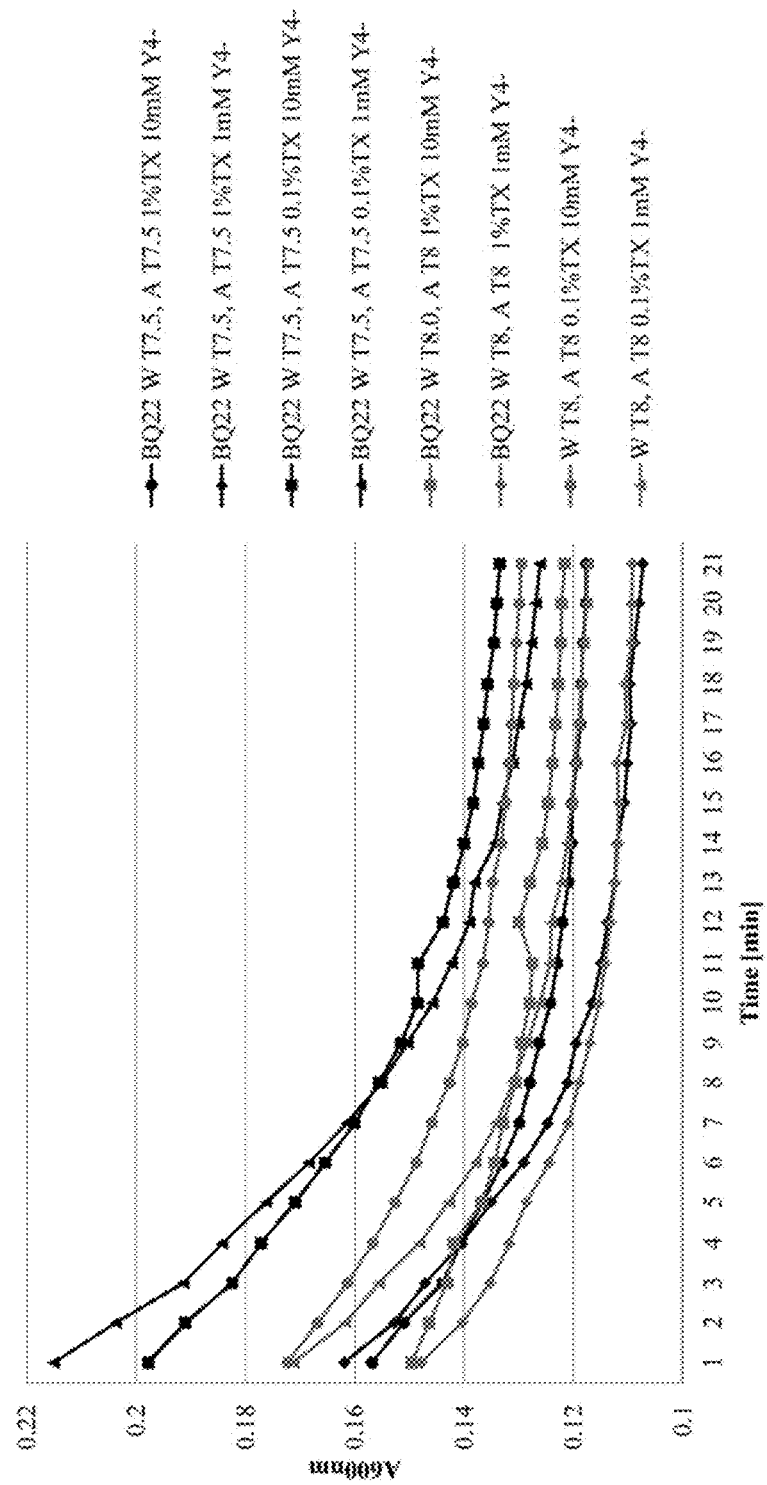

Figure 9

BQ22 lysin protein gene construct SEQ. ID No. 1 cggtgatgcggccggcacgatcgtcgccgtcgtagcgatcgagatctcgatccgcgaaatattatcaatcttatatgaattgtgagcggataacaattcccctctagaaataatttt
gttaactttaagaaggagatatacc-Atggg-catcatcatcatcatcatAGCCAGATACTCACAGATTCCAGATGTTCCTGCATGGGCTGACAAATCCGTTA
CTTATTTAGTTGATAAACAAGTATTGAGTGTTATCCAGATGTGGTTATCCAGATGGGACTTTGGTCAAGTGATACACTAGATAGACTTCTGCAGCAACAATT
ATGACTAAGGCTCTTGGTATACACATTGATTTAAATGCAAAAACCATCTTTAAAGATCACCAAAAACCACTGGGACCCCTTATATTGCCGCA
GCTGAAAGGCAGAATCATTAAAGGTGAAGGAAATGGAAATATTTAATCCTTCTGGAAAAGTTACTCGTGCTGCTATGGCTACTATGCTAC
TGAATGCATATAAACTACAAAATAAAACTAGACAATGGACAGATGGCTGCAACCAATAAATTCATAACCGCGTCAAGCTGCACAACTAACTGC
TACTTTAATTGATTTGAAAATTTCAGTTGGTACAGATAGTCATATAGTCATAGTAATCCTTTAGAAAATAAAACCATAATTATTGATCCGGACATGGTGCGAAGATCCTGAA
AAAAACAGATATGCTTCAATATAGTCATAGTAATCCTTTAGAAAATAAAACCATAATTATTGATCCGGACATGGTGCGAAGATCCTGAA
AAGACACAAAAGGATTACCTGAAAGTAAGATTGTACTAGACACTTCTTTACGTCTACAGGAAATTGCTGAAAACAATACACATTACAGTTT
TACTAACTCGTAAATCGTATACTGATACGACATGATCAAAAAGCTCTTTACAGGACGGAACGATGATCAAATCCAGGCGAT
ATCTTTATAAGTGTTCATCGAACATGTTAATGCAAATGGTAATGCAAAAGGGACCGAAACATACTACTATAATCTTCTAAATCTGAAAACAAT
CCTCATGTGGAAGAGAGTGTGTTTTAGCTGAAAAAAATTCAAACTCGATTAGTAGACGCTCTTCAAACACGTGATAGAGGCGTTAAACATGG
AGATCTTCATGTTATAAGAGAAATGACATGCGAAAGGCAACTTGCTTTATAGAAGTATATCAGTAGTTATCTAC
AGAAAACGGAAGGCAGATTGCTGCAGAAGCCATTTATGACGGGATTTTAGATTATTATCATGAACGAAAGGAAATAATGTATCTGAATATACGGC
TGTAActcgaggatccggctgctaacaaagcccgaaaggaagctgagttggctgctgccaccgctgagcaataactagcataaccccttggggcctctaaacgggtcttgaggggttttttg

---

☐ 6x His tag region catcatcatcatcatcat SEQ ID No: 5

☐ TATA Box

☐ lac operator gggaattgtgagcggataacaatt SEQ ID NO: 6

Underline T7 promoter taatacgactcactataggg SEQ ID No: 7

LYSIN AGENT AND METHOD OF USE FOR DIAGNOSTIC TESTING

GOVERNMENT INTEREST

The subject matter of this disclosure was made with support from the United States Department of Homeland Security (DHS). The Government of the United States of America has certain rights in this invention.

SEQUENCE LISTING

The instant application contains a Sequence Listing which has been submitted in ASCII format via EFS-Web and is hereby incorporated by reference in its entirety. The ASCII copy is named DHS-056 Sequence Listing.txt and is 6,660 bytes in size.

FIELD OF THE DISCLOSURE

The present disclosure relates to methods and compositions useful for identification of lytic enzymes. The disclosure relates to one or more novel peptidoglycan hydrolases that preferentially or specifically attacks the peptidoglycan cell wall of bacteria, and the use of the hydrolases as a lytic agent independently or in conjunction with molecular diagnostic testing for the rapid identification and lysing of *Bacillus anthracis* and certain related bacteria.

BACKGROUND OF THE INVENTION

A bacterial cell wall is a highly complex structure that encases the cell, provides it shape and maintains internal osmotic forces. The cell wall includes a thick layer of peptidoglycan, which is a heteropolysaccharide polymer comprised of subunits of alternating N-acetylglucosamine (Glc-NAc) and N-acetylmuramic (MurNAc) acid (also known as the glycan chain). The MurNAc moiety has a pentapeptide chain attached. Included subunits are linked by β1-4 glycosidic bonds and cross-linked via the peptide chains through alternating L- and D-amino acids. Various types of peptidoglycan are identified by the type of cross-linkage and the specific amino acid at the third position of the peptide chain. *Bacillus anthracis* has an A1γ type peptidoglycan, with the "A" indicating cross-linkage between positions 3 and 4 in the peptide chain; "1" indicating that it is a direct cross-linkage; and the "γ" (gamma) indicating that the direct cross-linkage is between meso diaminopimelic acid residue (DAP) and the D-Ala in position 4. Recent studies (such as Candela, T. et al.; N-Acetyl-glucosamine Deacetylases Module the Anchoring of the Gamma-Glutamyl Capsule to the Cell Wall of *Bacillus Anthracis*. Microbial Drug Resistance. 2014, 20(3), 222-230) indicate a high level (e.g., 92%) of peptidoglycan modification by N-deacylation of GlcNAc residues. This modification is typically responsible for the cell wall's resistance to lytic enzymes such as lysozyme and mutanolysin. Candela, T. et al., also reported that the cross-linkage of peptidoglycan in *Bacillus anthracis* is higher than previously reported.

Peptidoglycan hydrolases are a diverse group of enzymes that cleave the cell wall at specific structural sites and are responsible for the highly-regulated cleavage of peptidoglycan during cell growth and division. Peptidoglycan hydrolases can be organized into 4 classes: (i) amidases, (ii) endopeptidases, (iii) glucosaminidases, and (iv) lysozymes, each of which cleaves a specific bond within the peptidoglycan or its fragments. Peptidoglycan hydrolases typically comprise a substrate binding domain and an activity domain. The activity of a particular peptidoglycan hydrolase (lysin) may be dependent on one or both of these domains. Exogenous application of some lysin proteins to bacterial cells results in hydrolysis of peptidoglycan, and cell lysis due to osmotic shock.

SUMMARY OF THE INVENTION

In one or more embodiments, novel peptidoglycan hydrolase lytic enzymes are described. A vector comprising the nucleic acid molecule having of SEQ ID No: 1 is also described in one or more embodiments. One or more embodiments of the disclosure include an isolated, and/or purified nucleic acid molecule encoding a polypeptide having peptidoglycan hydrolase activity, a fragment or variant or derivative thereof or a fusion of the polypeptide, fragment, variant, or derivative, a host cell containing a nucleic acid molecule or a vector. One or more diagnostic substances including one or more polypeptides, fragments or variants or derivatives thereof, or one or more fusions of the polypeptide, fragment, variant, or derivative, are also described. One or more diagnostic assays including a polypeptide having peptidoglycan hydrolase activity, a fragment or variant, or derivative thereof or a fusion of the polypeptide, fragment, variant, or derivative are also described.

In one or more embodiments, the present disclosure describes: (1) creating an in-silico method to identify lysin(s) with predicted peptidoglycan hydrolytic activity against an intact cell wall of *Bacillus anthracis*. In one or more embodiments, methods to identify potential *Bacillus anthracis* lysin candidates by sequence similarity to known lysin proteins from bacteriophage, prokaryotic (including, but not limited to gram positive or gram negative), and eukaryotic organisms, and to screen the identified lysins for usage conditions are described. One or more lytic peptides having high activity against the intact *Bacillus anthracis* cell wall through the design and implementation of a turbidity reduction assay are described. One or more methods of purifying lysin proteins through an epitope tag, demonstrating the activity of the purified protein against whole cells of *Bacillus anthracis* is also described.

The present disclosure further describes one of more embodiments of the use of a *Bacillus anthracis* peptidoglycan hydrolase as a *Bacillus anthracis* lytic agent independently or in conjunction with molecular diagnostic tests intended for the rapid identification of *Bacillus anthracis*.

One or more methods are described for selecting a lysin agent for use in molecular diagnostic testing, including analyzing genome databases for *Bacillus anthracis* and near neighbors, selecting candidate genes encoding potential lytic enzymes based on conserved amino acid motifs as determined in peptidoglycan hydrolases, cloning the candidate genes in an expression vector, isolating proteins thereof, and testing the isolated protein for lytic activity against *Bacillus anthracis*, and selecting among the candidate genes for those which encode proteins with demonstrated lytic activity for further optimization of lysis conditions. In one or more embodiments, a vector construct comprising the sequence of SEQ ID NO: 1 and methods for making the lysin polypeptide BQ22 are also described.

In one or more embodiments, this disclosure further describes isolating and/or purifying (e.g., substantially purified, sufficiently pure for use in lysing cells) a DNA molecule comprising a nucleotide sequence encoding a polypeptide comprising the amino acid sequence of SEQ ID NO: 2; the polypeptide has peptidoglycan hydrolase activity.

In one or more embodiments, the present disclosure is further directed to a method for producing a polypeptide designated as BQ22 having peptidoglycan hydrolase activity. In one more embodiments, the method can be comprised of: introducing into an expression vector a nucleotide sequence comprising the sequence of SEQ ID NO: 1, the resulting recombinant vector comprising a nucleotide sequence encoding a protein having the amino acid sequence of SEQ ID NO: 2, the nucleotide sequence operably linked to at least one DNA sequence that controls expression of the BQ22 protein. In one or more embodiments, the recombinant vector is transformed into a host cell, thereby forming a recombinant host cell; the recombinant host cell is cultured under conditions suitable for expression of the lysin protein from the DNA molecule encoding the protein, such that BQ22 polypeptide is produced and the BQ22 polypeptide is isolated as a purified protein. In one or more embodiments, the recited order is the order in which the method is performed.

In one or embodiments, the present disclosure is further directed to a method for decontaminating and/or disinfecting a surface or area or object contaminated with *Bacillus anthracis* and certain related bacteria comprising contacting the surface or area or object with isolated polypeptide, fragment or variant, or derivative thereof or a fusion of the polypeptide, fragment, variant, or derivative having peptidoglycan hydrolase activity.

According to a first aspect, the present disclosure provides a recombinant nucleic acid comprising a nucleotide sequence encoding a polypeptide comprising the amino acid sequence of SEQ ID NO: 2, or a fragment, variant, or derivative thereof or a fusion of the polypeptide, fragment, variant, or derivative.

In one or more embodiments, the nucleotide sequence of the recombinant nucleic acid is operably linked to one or more control sequences.

In one or more embodiments, the one or more control sequences is selected from a group consisting of: a promoter, a transcriptional start signal, a transcriptional stop signal, a translational start signal, and a translational stop signal.

In one or more embodiments, the polypeptide comprising the amino acid sequence of SEQ ID NO: 2, or a fragment, variant, derivative or fusion thereof comprises a polypeptide tag.

In one or more embodiments, the polypeptide tag is a poly-histidine tag.

In one or more embodiments, the poly-histidine tag is a hexa-histidine tag.

In one or more embodiments, the nucleotide sequence encoding a polypeptide comprising the amino acid sequence of SEQ ID NO: 2, or a fragment, variant, or derivative thereof or a fusion of the polypeptide, fragment, variant, or derivative, comprises SEQ ID NO: 1.

According to a second aspect, the present disclosure provides a vector comprising a recombinant nucleic acid comprising a nucleotide sequence encoding a polypeptide comprising the amino acid sequence of SEQ ID NO: 2, or a fragment, variant, derivative thereof or a fusion of the polypeptide, fragment, variant, or derivative.

In one or more embodiments, the nucleotide sequence of the recombinant nucleic acid is operably linked to one or more control sequences.

In one or more embodiments, the one or more control sequences is selected from a group consisting of: a promoter, a transcriptional start signal, a transcriptional stop signal, a translational start signal, and a translational stop signal.

In one or more embodiments, the polypeptide comprising the amino acid sequence of SEQ ID NO: 2, or a fragment, variant, derivative or fusion thereof comprises a polypeptide tag.

In one or more embodiments, the polypeptide tag is a poly-histidine tag.

In one or more embodiments, the poly-histidine tag is a hexa-histidine tag.

In one or more embodiments, the nucleotide sequence encoding a polypeptide comprising the amino acid sequence of SEQ ID NO: 2, or a fragment, variant, or derivative thereof or a fusion of the polypeptide, fragment, variant, or derivative, comprises SEQ ID NO: 1.

According to a third aspect, the present disclosure provides a host cell transformed with a vector comprising a recombinant nucleic acid comprising a nucleotide sequence encoding a polypeptide comprising the amino acid sequence of SEQ ID NO: 2, or a fragment, variant, derivative thereof or a fusion of the polypeptide, fragment, variant, or derivative.

In one or more embodiments, the nucleotide sequence of the recombinant nucleic acid is operably linked to one or more control sequences.

In one or more embodiments, the one or more control sequences is selected from a group consisting of: a promoter, a transcriptional start signal, a transcriptional stop signal, a translational start signal, and a translational stop signal.

In one or more embodiments, the polypeptide comprising the amino acid sequence of SEQ ID NO: 2, or a fragment, variant, derivative or fusion thereof comprises a polypeptide tag.

In one or more embodiments, the polypeptide tag is a poly-histidine tag.

In one or more embodiments, the poly-histidine tag is a hexa-histidine tag.

In one or more embodiments, the nucleotide sequence encoding a polypeptide comprising the amino acid sequence of SEQ ID NO: 2, or a fragment, variant, or derivative thereof or a fusion of the polypeptide, fragment, variant, or derivative, comprises SEQ ID NO: 1.

According to a fourth aspect, the present disclosure provides for an isolated polypeptide comprising the amino acid sequence of SEQ ID NO: 2, or a fragment, variant, derivative thereof or a fusion of the polypeptide, fragment, variant, or derivative, the polypeptide having peptidoglycan hydrolase activity According to a fifth aspect, the present disclosure provides a method for producing a polypeptide with peptidoglycan hydrolase activity, comprising (a) providing a host cell comprising a vector comprising a nucleotide sequence encoding the polypeptide; and (b) culturing the host cell under culturing conditions; and (c) isolating the polypeptide, wherein the polypeptide comprises the amino acid sequence of SEQ ID NO: 2.

In one or more embodiments, the nucleotide sequence of the recombinant nucleic acid is operably linked to one or more control sequences.

In one or more embodiments, the one or more control sequences is selected from a group consisting of: a promoter, a transcriptional start signal, a transcriptional stop signal, a translational start signal, and a translational stop signal.

In one or more embodiments, the polypeptide comprising the amino acid sequence of SEQ ID NO: 2, or a fragment, variant, derivative or fusion thereof comprises a polypeptide tag.

In one or more embodiments, the polypeptide tag is a poly-histidine tag.

In one or more embodiments, the poly-histidine tag is a hexa-histidine tag.

In one or more embodiments, the nucleotide sequence encoding a polypeptide comprising the amino acid sequence of SEQ ID NO: 2, or a fragment, variant, or derivative thereof or a fusion of the polypeptide, fragment, variant, or derivative, comprises SEQ ID NO: 1.

According to a sixth aspect, the present disclosure provides a method for selecting a candidate lysin polypeptide for molecular diagnostic testing comprising (a) culturing a host cell comprising a vector comprising a nucleic acid sequence encoding the candidate lysin polypeptide, wherein the nucleic acid sequence is from a library of polynucleotide fragments; and (b) expressing the candidate lysin polypeptide under conditions in which a nucleic acid molecule encoding the candidate lysin polypeptide is expressed; and (c) isolating the candidate lysin polypeptide; and (d) incubating the candidate lysin polypeptide with a bacteria; and (e) selecting the nucleic acid sequence which encodes the candidate lysin polypeptide which exhibits peptidoglycan hydrolase activity against the bacteria.

In one or more embodiments, the library of polynucleotides is derived from sequences identified in a genome database by searching for nucleic acid sequences having at least 50% identity with a nucleic acid sequence of a model lytic enzyme.

In one or more embodiments, the library of polynucleotides is derived from sequences identified in a genome database by searching for nucleic acid sequences having at least 50% similarity with a nucleic acid sequence of a model lytic enzyme.

In one or more embodiments, the library of polynucleotides is derived from sequences identified in a genome database by searching for nucleic acid sequences having at least 60% identity with a nucleic acid sequence of a model lytic enzyme.

In one or more embodiments, the library of polynucleotides is derived from sequences identified in a genome database by searching for nucleic acid sequences having at least 60% similarity with a nucleic acid sequence of a model lytic enzyme.

In one or more embodiments, the library of polynucleotides is derived from sequences identified in a genome database by searching for nucleic acid sequences having between 70%-90% identity with a nucleic acid sequence of a model lytic enzyme.

In one or more embodiments, the library of polynucleotides is derived from sequences identified in a genome database by searching for nucleic acid sequences having between 70%-90% similarity with a nucleic acid sequence of a model lytic enzyme.

In one or more embodiments, the library of polynucleotides is derived from sequences identified in a genome database by searching for nucleic acid sequences having at least 90% identity with a nucleic acid sequence of a model lytic enzyme.

In one or more embodiments, the library of polynucleotides is derived from sequences identified in a genome database by searching for nucleic acid sequences having at least 90% similarity with a nucleic acid sequence of a model lytic enzyme.

In one or more embodiments, the library of polynucleotides is derived from sequences identified in a genome database by searching for nucleic acid sequences having at least 95% identity with a nucleic acid sequence of a model lytic enzyme.

In one or more embodiments, the library of polynucleotides is derived from sequences identified in a genome database by searching for nucleic acid sequences having at least 95% similarity with a nucleic acid sequence of a model lytic enzyme.

In one or more embodiments, the library of polynucleotides is derived from sequences identified in a genome database by searching for amino acid sequences encoded by the sequences having at least 50% identity with an amino acid sequence of a model lytic enzyme.

In one or more embodiments, the library of polynucleotides is derived from sequences identified in a genome database by searching for amino acid sequences encoded by the sequences having at least 50%0 similarity with an amino acid sequence of a model lytic enzyme.

In one or more embodiments, the library of polynucleotides is derived from sequences identified in a genome database by searching for amino acid sequences encoded by the sequences having at least 60% identity with an amino acid sequence of a model lytic enzyme.

In one or more embodiments, the library of polynucleotides is derived from sequences identified in a genome database by searching for amino acid sequences encoded by the sequences having at least 60% similarity with an amino acid sequence of a model lytic enzyme.

In one or more embodiments, the library of polynucleotides is derived from sequences identified in a genome database by searching for amino acid sequences encoded by the sequences having between 70%-90% similarity with an amino acid sequence of a model lytic enzyme.

In one or more embodiments, the library of polynucleotides is derived from sequences identified in a genome database by searching for amino acid sequences encoded by the sequences having between 70%-90% identity with an amino acid sequence of a model lytic enzyme.

In one or more embodiments, the library of polynucleotides is derived from sequences identified in a genome database by searching for amino acid sequences encoded by the sequences having at least 90% identity with an amino acid sequence of a model lytic enzyme.

In one or more embodiments, the library of polynucleotides is derived from sequences identified in a genome database by searching for amino acid sequences encoded by the sequences having at least 90% similarity with an amino acid sequence of a model lytic enzyme.

In one or more embodiments, the library of polynucleotides is derived from sequences identified in a genome database by searching for amino acid sequences encoded by the sequences having at least 95% identity with an amino acid sequence of a model lytic enzyme.

In one or more embodiments, the library of polynucleotides is derived from sequences identified in a genome database by searching for amino acid sequences encoded by the sequences having at least 95% similarity with an amino acid sequence of a model lytic enzyme.

In one or more embodiments, the bacteria is prokaryote.

In one or more embodiments, the prokaryote is a gram-positive bacteria.

In one or more embodiments, the gram-positive bacteria is a *Bacillus* species.

In one or more embodiments, the *Bacillus* species is *Bacillus anthracis*.

In one or more embodiments, the prokaryote is a gram-negative bacteria.

In one or more embodiments, the gram-negative bacteria is a *Yersinia* species.

In one or more embodiments, the *Yersinia* species is *Yersinia pestis*.

According to a seventh aspect, the present disclosure provides a method for diagnosing the presence or absence of bacteria in a sample comprising (a) providing a sample of the bacteria; and (b) incubating the sample of the bacteria in the presence of an isolated polypeptide having peptidoglycan hydrolase activity, and (c) contacting the sample and the isolated polypeptide having peptidoglycan hydrolase activity with at least a first and a second oligonucleotide primer under conditions sufficient to provide polymerase-based nucleic acid amplification; and (d) detecting In one or more embodiments, the bacteria is prokaryote.

In one or more embodiments, the bacteria is prokaryote.

In one or more embodiments, the prokaryote is a gram-positive bacteria.

In one or more embodiments, the gram-positive bacteria is a *Bacillus* species.

In one or more embodiments, the *Bacillus* species is *Bacillus anthracis*.

In one or more embodiments, the prokaryote is a gram-negative bacteria.

In one or more embodiments, the gram-negative bacteria is a *Yersinia* species.

In one or more embodiments, the *Yersinia* species is *Yersinia pestis*.

In one or more embodiments, the polymerase-based nucleic acid amplification is quantitative polymerase chain reaction (QPCR).

In one or more embodiments, the polypeptide comprises the amino acid sequence of SEQ ID NO: 2, or a fragment, variant, derivative thereof, or a fusion of the polypeptide, fragment, variant, or derivative.

According to an eighth aspect, the present disclosure provides a method for lysing bacteria comprising (a) providing a sample of the bacteria; and (b) preparing an isolated polypeptide having peptidoglycan hydrolase activity; and (c) incubating the isolated polypeptide with the bacteria.

In one or more embodiments, the bacteria is prokaryote.

In one or more embodiments, the prokaryote is a gram-positive bacteria.

In one or more embodiments, the gram-positive bacteria is a *Bacillus* species.

In one or more embodiments, the *Bacillus* species is *Bacillus anthracis*.

In one or more embodiments, the prokaryote is a gram-negative bacteria.

In one or more embodiments, the gram-negative bacteria is a *Yersinia* species.

In one or more embodiments, the *Yersinia* species is *Yersinia pestis*.

In one or more embodiments, the polypeptide comprises the amino acid sequence of SEQ ID NO: 2, or a fragment, variant, derivative thereof, or a fusion of the polypeptide, fragment, variant, or derivative.

According to an ninth aspect, the present disclosure provides a method for decontaminating a surface or room or area or object contaminated with bacteria comprising contacting the surface or room or area or object with a composition comprising an isolated polypeptide having peptidoglycan hydrolase activity against the bacteria.

In one or more embodiments, the bacteria is prokaryote.

In one or more embodiments, the prokaryote is a gram-positive bacteria.

In one or more embodiments, the gram-positive bacteria is a *Bacillus* species.

In one or more embodiments, the *Bacillus* species is *Bacillus anthracis*.

In one or more embodiments, the prokaryote is a gram-negative bacteria.

In one or more embodiments, the gram-negative bacteria is a *Yersinia* species.

In one or more embodiments, the *Yersinia* species is *Yersinia pestis*.

In one or more embodiments, the polypeptide comprises the amino acid sequence of SEQ ID NO: 2, or a fragment, variant, derivative thereof, or a fusion of the polypeptide, fragment, variant, or derivative.

According to an tenth aspect, the present disclosure provides a method for disinfecting a surface or room or area or object contaminated with bacteria comprising contacting the surface or room or area or object with a composition comprising an isolated polypeptide having peptidoglycan hydrolase activity against the bacteria.

In one or more embodiments, the bacteria is prokaryote.

In one or more embodiments, the prokaryote is a gram-positive bacteria.

In one or more embodiments, the gram-positive bacteria is a *Bacillus* species.

In one or more embodiments, the *Bacillus* species is *Bacillus anthracis*.

In one or more embodiments, the prokaryote is a gram-negative bacteria.

In one or more embodiments, the gram-negative bacteria is a *Yersinia* species.

In one or more embodiments, the *Yersinia* species is *Yersinia pestis*.

In one or more embodiments, the polypeptide comprises the amino acid sequence of SEQ ID NO: 2, or a fragment, variant, derivative thereof, or a fusion of the polypeptide, fragment, variant, or derivative.

According to an eleventh aspect, the present disclosure provides a method for treating a bacterial infection comprising administering to a subject in need of such treatment, a composition comprising an antibiotic that is effective against the bacteria and an isolated polypeptide having peptidoglycan hydrolase activity against the bacteria.

In one or more embodiments, the bacteria is prokaryote.

In one or more embodiments, the prokaryote is a gram-positive bacteria.

In one or more embodiments, the gram-positive bacteria is a *Bacillus* species.

In one or more embodiments, the *Bacillus* species is *Bacillus anthracis*.

In one or more embodiments, the prokaryote is a gram-negative bacteria.

In one or more embodiments, the gram-negative bacteria is a *Yersinia* species.

In one or more embodiments, the *Yersinia* species is *Yersinia pestis*.

In one or more embodiments, the polypeptide comprises the amino acid sequence of SEQ ID NO: 2, or a fragment, variant, derivative thereof, or a fusion of the polypeptide, fragment, variant, or derivative.

In one or more embodiments, the antibiotic is polymyxin.

In one or more embodiments, the polymyxin is administered at a concentration that is non-toxic to the subject.

BRIEF DESCRIPTION OF THE DRAWINGS

The accompanying drawings illustrate one or more embodiments of the present disclosure and, together with the detailed description and examples sections, serve to explain the principles and implementations of the disclosure. While the foregoing disclosure describes one or more embodiments of the invention, it should be clearly understood that the disclosure is by way of illustration and example only, and is not limiting.

Figure 1:
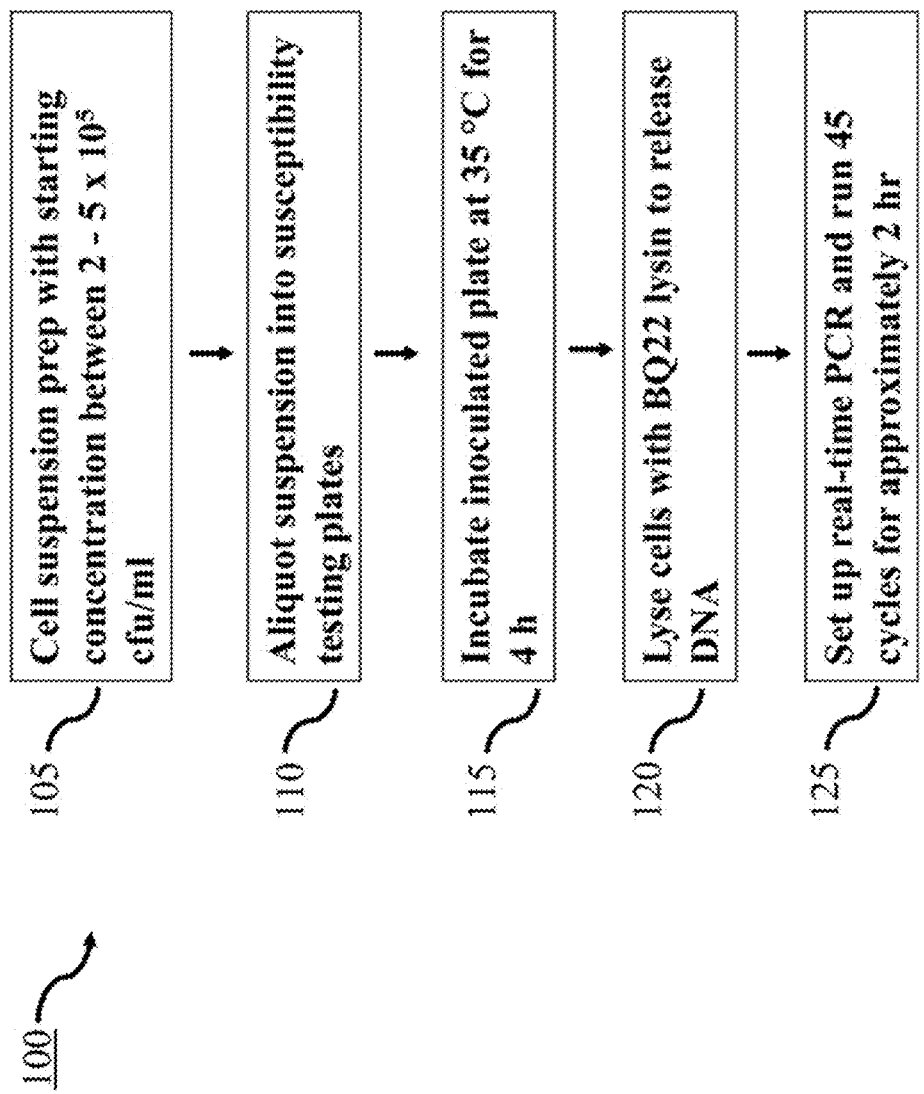
FIG. 1 is a diagrammatic view showing the steps in a rapid antimicrobial susceptibility assay based on the use of one or more embodiments.

FIG. 7 is a graph illustrating lytic activity of IMAC purified BQ22 and BQ23 against *Bacillus anthracis* Sterne.

FIG. 8 is a graph illustrating activity of IMAC purified BQ22 is against EDTA-treated *Y. pestis*.

FIG. 9 illustrates the DNA sequence features of a vector construct for BQ22.

DETAILED DESCRIPTION

The following terminology is provided for convenience and should not be taken to imply that the terminology is being redefined herein to be restricted to any specific characteristics, features, or aspects of the invention with which that terminology is associated.

For purposes of the present disclosure, "peptidoglycan"—refers to a heteropolymer consisting of N-acetylglucosamine and N-acetylmuramic acid subunits linked by β1-4 glycosidic bonds and cross-linked by short peptides, forming a cell wall, which generally surrounds the cell, maintains cell shape, protects the cell from rupture due to internal turgor pressure, and serves as a platform for attachment of various proteins.

For purposes of the present disclosure, "lysin" refers to an enzyme that has the ability to hydrolyse bacterial cell walls and exhibits peptidoglycan hydrolytic activity. Lysins may optionally include at least one enzymatically active domain (EAD) having at least one of the following activities: amidases, muramidases, glucosaminidases, and endopeptidases. In addition, the lysins may also optionally include regions that are enzymatically inactive, including, but not limited to cell wall-binding domains (CBDs), which may serve to bind to the bacterial cell wall. Lysins may optionally contain two or more CBDs. Lysins also may optionally refer to enzymes with at least one enzymatically active domain but no CBD. Generally, cell wall-binding domains bind to specific components on the cross-linked peptidoglycan heteropolymer that form the bacterial cell wall. In one or more non-limiting examples, the cell wall binding domain is a peptidoglycan binding domain and binds to the bacteria's peptidoglycan structure. In one or more non-limiting examples, an amino acid linker region may optionally be present to connect the lysin's different domains.

For purposes of the present disclosure, "amidase" refers to any peptidoglycan hydrolytic enzyme that hydrolyzes the muramic acid-D-alanine bond linking the glycan strand to the peptide subunit.

For purposes of the present disclosure, "lysozyme" refers to any peptidoglycan hydrolytic enzyme that hydrolyzes the β1-4 glycosidic bond between N-acetylmuramic acid and N-acetylglucosamine.

For purposes of the present disclosure, "transglycosylase" refers any peptidoglycan hydrolytic enzyme that hydrolyzes the β1-4 glycosidic bond between N-acetylmuramic acid and N-acetylglucosamine resulting in the formation of an anhydromuramoyl residue.

For purposes of the present disclosure, "glucosaminidase" refers to any peptidoglycan hydrolytic enzyme that hydrolyzes the β1-4 glycosidic bond between N-acetylglucosamine and N-acetylmuramic acid.

For purposes of the present disclosure, "endopeptidase" refers to any peptidoglycan hydrolytic enzyme that hydrolyzes any of the bonds within the peptide subunits cross-linking glycan strands.

For purposes of the present disclosure, "PlyG" refers to a *Bacillus* phage gamma endolysin amidase (Schuch, R. et al.; A Bacteriolytic Agent that Detects and Kills *Bacillus Anthracis. Nature.* 2002, 418, 884-889).

For purposes of the present disclosure, "PlyPH" refers to a *Bacillus* phage endolysin lysozyme (Yoong, P. et al.; PlyPH, a Bacteriolytic Enzyme with a Broad PH Range of Activity and Lytic Action again *Bacillus Anthracis. J. Bacteriol.* 2006, 188, 2711-2714). A non-limiting example of PlyPH may include BCZK2532.

For purposes of the present disclosure, "similarity" refers to the degree of resemblance between two or more amino acid, peptide, polypeptide, or protein sequences or two or more nucleic acid, DNA, nucleotide, or polynucleotide sequences, as determined by the match between strings of such sequences. As a non-limiting example, a peptide fragment, or the amino acid sequence within a region of a full length protein is similar to that of another as further defined by the degree to which amino acid residues within said regions are conserved.

For purposes of the present disclosure, "identity" refers to the condition of one particular amino acid, a peptide fragment, or the amino acid sequence within a region of a full length protein being the same to that of another amino acid, a peptide fragment, or the amino acid sequence within a region of a full length protein, as determined by the match between strings of such sequences, after aligning the sequences and inserting gaps between the sequence residues.

Identity and similarity may be determined by a variety of methods including, but not limited to, those described in Dölz, R.; GCG: Comparison of Sequences. In *Methods in Molecular Biology Computer Analysis of Sequence Data, Part I, Vol.* 24: Humana Press, Totowa, 1994; pp. 65-82; Dölz, R; GCG: Production of Multiple Sequence Alignment. In *Methods in Molecular Biology Computer Analysis of Sequence Data, Part I, Vol* 24; Humana Press, Totowa, 1994; pp. 83-99; and Carrillo, H., et al.; The Multiple Sequence Alignment Problem in Biology. *SIAM J. App. Math.* 1988, 48.5, 1073-1082.

Methods to determine identity may generally be designed to give the largest match between the sequences tested. Methods to determine identity and similarity may be codified in a variety of computer programs including, but not limited to, GCG program package (Devereux, J. et al.; A Comprehensive Set of Sequence Analysis Programs for the VAX. *Nucleic Acids Research.* 1984, 12.1, 387-395), Best- Fit, BLASTP, BLASTN, and FASTA (Altschul, S. F. et al.; Basic Local Alignment Search Tool. *J. Mol. Biol.* 1990, 215, 403-410). The BLAST X program is publicly available from NCBI and other sources (Altschul, S. F. et al.; Basic Local Alignment Search Tool. *J. Mol. Riol.* 1990, 215, 403-410). The Smith Waterman algorithm may optionally also be used to determine identity.

Parameters for polypeptide sequence comparison may include those described in the following: Needleman, S. B. et al.; A General Method Applicable to the Search for Similarities in the Amino Acid Sequence of Two Proteins. *J. Mol. Biol.* 1970, 48, 443-453; Henikoff, S., et al.; Amino Acid substitution Matrices from Protein Blocks. *Proc. Natl. Acad. Sci. USA.* 1992, 89, 10915-10919. As a non-limiting example, a program useful with these parameters is the publicly available "Ogap" program from Genetics Computer Group, located in Madison, Wis.

Parameters for nucleic acid comparison may include those described in the following: Pearson, W. R., et al; Improved Tools for Biological Sequence Comparison. *Proc. Natl. Acad. Sci. USA.* 1988, 85, 2444-2448.

Optionally, in determining the degree of amino acid similarity, conservative amino acid substitutions may also be considered. Conservative amino acid substitutions generally refer to the interchangeability of residues having similar side chains and usually without affecting function. For example, a group of amino acids having aliphatic side chains may include glycine, alanine, valine, leucine, and isoleucine; a group of amino acids having aliphatic-hydroxyl side chains may include serine and threonine; a group of amino acids having amide-containing side chains may include asparagine and glutamine; a group of amino acids having aromatic side chains may include phenylalanine, tyrosine, and tryptophan; a group of amino acids having basic side chains may include lysine, arginine, and histidine; and a group of amino acids having sulphur-containing side chains may include cysteine and methionine. Conservative amino acids substitution groups include, but are not limited to, valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. In embodiments, the amino acid change may be conservative. Conservative substitutions for naturally occurring amino acids include, but are not limited to: alanine to serine; arginine to lysine; asparagine to glutamine or histidine; aspartate to glutamate; cysteine to serine or alanine; glutamine to asparagine; glutamate to aspartate; glycine to proline; histidine to asparagine or glutamine; isoleucine to leucine or valine; leucine to isoleucine or valine; lysine to arginine, glutamine or glutamate; methionine to leucine or isoleucine; phenylalanine to methionine, leucine or tyrosine; serine to threonine; threonine to serine; tryptophan to tyrosine; tyrosine to tryptophan or phenylalanine; and, valine to isoleucine or leucine.

For purposes of this disclosure, a nucleic acid sequence or nucleotide sequence is a series of letters indicating the order of nucleotides or nucleic acids within a DNA (using GACT) or RNA molecule (using GACU). The DNA or RNA molecule may be single or double stranded, and may be genomic, recombinant, messenger RNA (mRNA) or complementary DNA (cDNA).

For purposes of this disclosure, an amino acid sequence or peptide sequence is a series of letters indicating the order of amino acids within a polypeptide or protein molecule.

For purposes of this disclosure, a nucleic acid construct is a nucleic acid molecule that may be isolated from a naturally occurring gene or which may be modified to contain segments of nucleic acids which are combined or juxtaposed in a manner which would not otherwise exist in nature. Optionally, a nucleotide sequence present in a nucleic acid construct may be operably linked to one or more control sequences, which direct the transcription or expression of messenger RNA that the cell machinery (ribosome) then translates into a peptide or polypeptide in a cell.

For purposes of this disclosure, a control sequence may include all DNA sequences which are necessary, for the expression of a protein. At a minimum, the control sequences may include a promoter and transcriptional and translational start and stop signals. Optionally, a promoter represented by a nucleotide sequence present in a nucleic acid construct may be operably linked to another nucleotide sequence encoding a peptide or polypeptide.

For purposes of this disclosure, a nucleic acid sequence is operably linked when a control sequence is appropriately placed at a position relative to the nucleotide sequence coding for a polypeptide so the control sequence directs the transcription/production/expression of the peptide or polypeptide of the invention in a cell. Operably linked may also optionally define a configuration in which a nucleic acid sequence is appropriately placed at a position relative to another nucleic acid sequence that codes for a functional domain such that a chimeric polypeptide may be encoded in a cell.

For purposes of this disclosure, the expression of a protein may include any step involved in the production of the peptide or polypeptide including, but not limited to, transcription, post-transcriptional modification, translation, post-translational modification and secretion.

For purposes of this disclosure, a transformation refers to a permanent or transient genetic change induced in a cell following the incorporation of new DNA (i.e. DNA exogenous to the cell). When the cell is a bacterial cell, the term usually refers to an extra-chromosomal, self-replicating vector such as a plasmid which harbors a selectable antibiotic resistance.

For purposes of this disclosure, an expression vector may be any molecular construct which may be conveniently subjected to recombinant DNA procedures and can bring about the expression of a nucleotide sequence encoding a polypeptide of the invention in a cell. A promoter refers to a nucleic acid fragment that functions to control the transcription of one or more genes or nucleic acids, located upstream with respect to the direction of transcription of the transcription initiation site of the gene. The promoter region is related to the binding site identified by the presence of a sequence that is recognized as a binding site by DNA-dependent RNA polymerase, transcription initiation sites, and any other DNA sequences, including, but not limited to, transcription factor binding sites, repressor and activator protein binding sites, and any other sequences of nucleotides that acts directly or indirectly to regulate the amount of transcription from the promoter. Within the context of the invention, a promoter preferably ends at nucleotide-1 of the transcription start site (TSS).

For purposes of this disclosure, a polypeptide is any peptide, oligopeptide, polypeptide, amino acid gene product, expression product, or protein. A polypeptide may be a naturally occurring or synthetic molecule.

For purposes of this disclosure, a fusion protein is an expression product resulting from the fusion of two or more nucleic acid constructs, and may include, but is not limited to a fusion of two or more polypeptides, fragment, variant, or derivative thereof corresponding to the two or more nucleic acid constructs.

In one or more embodiments, a candidate lysin is identified by comparing DNA or protein sequences of a bacteria with sequences of a model lytic enzyme capable of targeting moieties in the cell wall of a bacteria and selecting sequences having an identity greater than about 50% or similarity greater than about 60% with the sequences of the entire model lytic enzyme or selected portions thereof which may be associated with the lytic activity of the enzyme.

Non-limiting examples of model lytic enzymes include small phage-produced proteins responsible for lysis of an infected host cell, such as those described in Borysowski, J. et al.; Bacteriophage Endolysins as a Novel Class of Antibacterial Agents. 2006. *Exp. Biol. Med.* 231.4, 366-377. In one or more embodiments, model lytic enzymes optionally include one or more endolysins. An endolysin is a lyric enzyme or protein typically produced by a bacteriophage that degrades the infected bacterial cell wall, facilitating release of new bacteriophage from the infected bacterial cells at the end of the phage infection cycle. Usually, fully functional endolysins accumulate in the infected bacterial cytosol near the end of the phage infection cycle.

Comparisons can be performed using various approaches that allow computationally identifying candidate lysins as described herein.

For example, a comparison is performed by in silico computer searches of a bacteria's genome using the sequences of the model lytic enzyme as a parameter. Search tools include, but are not limited to, the Basic Local Alignment Search Tool (BLAST) from the National Institutes of Health. Several strategies can be employed for the computer searches. In one or more embodiments, the comparison by computer searches comprises performing an analysis of genome annotations to identify candidate genes encoding lytic proteins. Annotations also may optionally identify genes that function in bacterial cell wall synthesis and processing and may include lytic enzymes.

Another in silico approach for comparing can be performed by directly comparing DNA sequences of model lytic enzymes or by directly comparing the predicted amino acid sequences of such proteins to predicted sequences in targeted genomes.

A further exemplary in silico approach for comparing can be performed by predicting the protein structure of known lytic proteins based on their predicted or determined amino acid sequences, and then searching available sequence databases (e.g. DNA databases) for sequences that encode proteins of similar predicted structure. Successfully targeted genes will encode lysins that exhibit lytic activity against a targeted bacterial pathogen.

The comparisons can be performed by analysis based on local protein or DNA alignment studies that compare relatedness (identity and similarity) using a known sequence (e.g. model lytic protein and/or a portion thereof), or compilation of sequences (e.g. one or more model lytic protein and/or a portion thereof), used to search any available database (e.g. using BLAST) that contains genetic (DNA) or protein sequences or information to identify novel protein sequences.

A comparison can be performed between nucleotide sequences or between amino acid sequences of the model lytic enzyme and selected bacterial genomes. The comparison may be done by considering sequences covering the model lytic enzyme (e.g., the entire model lytic enzyme) or the one or more portions of the model lytic enzymes associated with the lytic activity of the model lytic enzyme. Those portions can include not only the lytic domain of the model lytic enzyme, but also additional domains responsible for protein stability, three-dimensional structure, and any other features associated with an active protein. Those portions can vary from one model enzyme to another. In embodiments, selected genome sequences from a bacteria at issue show at least 50% identity or 60% similarity or about a 50% similarity or about 60% identity in outcome. In other aspects, sequences with 70% to 90% identity or similarity or about 70% to 90% identity are selected. In further aspects, a sequence having at least 90% identity or similarity and in particular about 95% or higher identity or similarity are selected.

For example, in an embodiment, basic alignment and local basic alignments in programs such as Geneious 5.0.3 or ClustalW are used to look for specific similarities. Using default settings, proteins with pairwise identity of 50% or higher can be typically selected.

For example, in embodiments wherein BLAST is used, proteins with a "Total Score" of about 100 or more and/or an E value of 0.001 or lower are selected as candidate lysins.

In another aspect, identification includes performing a plurality of comparisons using the same, substantially the same, or different approaches. In some of those aspects, performing a plurality of comparisons using different approaches may identify candidate lysins that show less than 50% identity or 60% similarity to a model lytic enzyme or selected portions thereof that may be associated with lytic activity of the enzyme. In one or more embodiments, a search can be limited to direct DNA sequence comparisons that can limit the number of genes encoding these lytic proteins.

In other aspects of the invention, identifying candidate lysins is performed by doing a plurality of screen levels of the genome sequences of the lysins of interest. As a non-limiting example, a first screening of one or more genomes involves analysis of provisionally identified annotated genes encoding any of the four classes of lytic proteins, which optionally may include model lytic enzymes. Bacteria from which the identified genes may be obtained may include, but are not limited to bacterial, bacteriophage, prokaryotic, and eukaryotic. The second screen may optionally include a BLAST search of the one or more identified genes against gene sequences encoding these lytic proteins in bacteria that are closely related to the bacteria of interest. The third screen may optionally include a search for genes that have been implicated in cell wall biosynthesis or metabolism. The fourth screen may optionally include comparing the amino acid sequences encoded by the identified genes to the amino acid sequences of other lytic proteins. The fifth screen may optionally include a computational analysis of the amino acid sequences of other lytic proteins to identify specific structural characteristics of this class of proteins followed by a computational search of genomes to identify genes encoding proteins that may have similar structure. Bacteria from which the identified genes may be obtained may include, but are not limited to bacterial, bacteriophage, prokaryotic, and eukaryotic. As a non-limiting example, a small number of endolytic proteins have been structurally characterized, and the structures of portions of the proteins responsible for lytic activity have been identified, from which a search for similar structures encoded in the genomes of organisms of interest can be performed. Exemplary procedures for identifying candidate lysins are reported in the Examples of the present application.

Once a candidate lysin is identified, the candidate lysin can be tested for lytic activity on the same bacteria expressing the candidate lysin or on a bacteria related to the bacteria expressing the candidate lysin. In one or more embodiments, the gene coding for the candidate lysin can be amplified from a bacterial genome, cloned and expressed in an in vitro transcription (IVT) system. Exemplary procedures are illustrated in the Examples of the present application. In another embodiment, the identified candidate lysin is acquired from other sources such as transformed host cells.

In one or more embodiments, the candidate lysin is subjected to one or more tests, where the bacteria is exposed to the candidate lysin to determine the lytic activity of the candidate lysin on the bacteria. In a further embodiment, a first screen is provided by a spot test. Although this procedure can be performed with a substantially pure protein, or a purified protein, the procedure does not require purified protein. Additional procedures that may be used to detect lytic activity and to determine suitability as lysins include, but are not limited to, the lysis of the bacteria, a visible clearing or reduction of viable cells, or a decrease in the absorbance of a cellular suspension exposed to the lysin as recorded with a spectrophotometer.

Once one or more candidate genes are identified at each step, the genes can be to amplified from the bacterial genome of interest in a single set of experiments. In one or more embodiments, PCR primers suitable to amplify the genes of interest and facilitate their (immediate) cloning into a standard expression vector are used to stream-line the process. Additionally, several gene products can be tested simultaneously.

Additionally, where the amplification is performed from the genome of a bacteria other than the original bacteria expressing the enzyme, a factor that may be considered are codon preferences of the target microbe from which the gene is amplified relative to those where the amplification is performed. If codon preferences are significantly different between the original bacteria and the microbe from which the putative lytic protein gene is cloned and expressed, that gene may not be expressed to a desired level in the selected bacteria. Other approaches can be used in addition to or as an alternative to include, but are not limited to, an IVT system. These approaches include, but are not limited to, re-synthesizing the gene using chemical DNA synthesis to produce a gene that encodes the same protein amino acid sequence but that is optimized for expression in the recombinant organism system.

The candidate lysins that have a detectable lytic activity can be selected as lysins for one or more species of bacteria wherein the lytic activity has been tested or can be predicted based on genetic relationship.

The lysins obtained by one or more of the methods described comprise proteins that possess enzymatic and lytic activity that specifically damage cell walls and that destroy the bacterial target. Non-limiting examples of the lysins that may be obtained by methods disclosed are structurally related to lysozymes (also known as muramidase) or other model lytic proteins. These model lytic proteins are comprised of an N-terminal portion (domain) responsible for lytic activity and a C-terminal portion (domain) responsible for target recognition and binding. In various embodiments, the lysins obtained by these one or more of the methods described differ from lysozymes or other model lytic proteins because of their high specificity and ability to target a given bacteria or group of bacteria based on the chemical structure and linkage of cell wall components.

The lysins described in this disclosure differ from other lysins including, but not limited to model lytic proteins in that, under certain conditions, they are more efficacious than the model lytic proteins and are encoded by genes from the target bacteria's own genome. The lysins described herein may be comprised of lyric proteins which target specific moieties of the bacteria's cell wall and normally play a role in synthesizing and maintaining the peptidoglycan layer of a bacteria's cell wall. In general the lysins described in this disclosure are enzymes encoded by the target bacteria's own genes and are involved in cell wall biosynthesis and metabolism.

The lysins described in this disclosure are able to disrupt and destabilize the peptidoglycan cell wall of the bacteria expressing the lysin under suboptimal conditions for a bacteria to regulate lysin expression and/or activity, which may result in preventing the bacteria from maintaining osmotic equilibrium or which may otherwise impact the viability of the cell.

The suboptimal conditions for a bacteria to regulate lysin expression and/or activity may include, but are not limited to conditions where the concentrations of lysin obtained by one or more of the methods described is higher than the concentration of lysin produced by the targeted bacteria, which are not confined to the locations within the cells of the bacteria where they are normally expressed, absence of inhibitors, and other conditions. In one or more embodiments where the bacteria is a spore-forming bacteria, the conditions typically include any condition where the spore-forming bacteria are in a vegetative state. In other embodiments, non-appropriate conditions for a bacteria to regulate lysin expression and/or activity may include, but are not limited to providing a concentration of a lysin that is about 2:1 or greater than the concentration produced by the bacteria. In several embodiments, exposure of the bacteria to concentrations of a lytic protein described in this disclosure that are at least 2-3 orders of magnitude higher than the concentration normally produced by the bacteria or a bacteria that is genetically related to the bacteria expressing a lytic protein described in this disclosure, typically results in rapid cell lysis and death of the bacteria or the bacteria that is genetically related. A non-limiting example of concentrations of lysin normally produced by the bacteria includes production of very minute amounts at very specific locations within the bacterial cells.

The lysins described in this disclosure may kill or inhibit growth not only of the bacteria expressing the enzyme but also of genetically related bacteria.

Generally, genetically related bacteria express at least one protein that has a 50% or higher identity or a 60% or higher similarity or about a 50% or higher identity or about a 60% or higher similarity to a corresponding protein in another bacteria. As a non-limiting example, a first bacteria expressing a first lysin is related to a second bacteria expressing a second lysin, if the second protein has about a 50% or higher identity or a 60% or higher similarity to the first lysin. A closer genetic relationship is evidenced in some embodiments, by sequences showing a 70% to 90% identity or similarity or about 70% to 90% identity or similarity, sequences having at least 90% identity or similarity and in particular about 95% or higher identity or similarity between the bacteria.

For example, members of a subgroup of *Bacillus*, which includes *Bacillus anthracis*, are genetically related with a subset of *Bacillus* species. As a non-limiting example, *Bacillus cereus* is closely related but *Bacillus subtilis* is not as closely related to *Bacillus anthracis*. Similarly, *Yersinia*

*pestis* is very closely related to *Yersinia pseudotuberculosis* but not as closely related to *Yersinia enterocolitica*. *Burkholderia mallei* and *Burkholderia pseudomallei* are very closely related while neither is closely related to *Bacillus anthracis*.

The effectiveness of a lysin on a bacteria related to another bacteria expressing the lysin is correlated to how closely related the bacteria are. Accordingly, the higher the percentage identity/similarities between at least one lysin protein expressed by both of the bacteria, the higher the effectiveness of the lysin is expected.

Lytic and endolysin activity are forms of hydrolytic activity that damages or destroys specific linkages between cell wall moieties resulting in degradation of the cell wall and resulting bacterial cell death. Endolysins are produced by a bacteriophage during the bacterial lytic infection cycle and serve to disrupt the bacterial cell wall to release progeny phage. Both endolysin activity and lytic activity modify, alter, or damage bacterial cell walls. Lytic proteins may be derived from non-phage sources. These proteins normally function, in vive, to regulate cell wall synthesis and maintenance, but may also be used to generate unregulated breaks in the cell wall, usually resulting in disruption of growth and also cell death. Typically, lytic and endolysin activity is associated with a protein that is a member of one of four classes of peptidoglycan hydrolases and possibly, some as yet uncharacterized proteins.

Differences in activity between lytic enzymes may be measured using various technical approaches. As a non-limiting example, the difference in activity between a model lytic enzyme and a lysin or between two lysins described in this disclosure may be measured by applying the same concentration of lysin to the same number of bacterial cells in the same reaction volume and incubating under the optimal conditions for each lysin for a specific period of time. The number of surviving cells is then measured by plating the treated cells on agar plates and counting the number of colonies that grow on the plates. If identical concentrations of the two proteins result in a difference in the number of surviving colonies the relative effectiveness of the lysins may be determined. As a non-limiting example, if treatment with a phage endolysin results in 100 colonies growing on the test plate and 0 colonies growing on the bacterial lysin test plate, then the bacterial lytic protein is at least 100 times or two orders of magnitude (10×10) more effective than the phage endolysin infection cycle.

In one or more embodiments, the lysins described in this disclosure are recombinant proteins, which can be identical or modified with respect to the original enzyme. As a non-limiting example, a recombinant lysin may comprise a six histidine residue end tag to facilitate rapid purification of the protein. Other non-limiting examples include those modifications to improve solubility or other features of the lysins. As a non-limiting example, in some embodiments lytic proteins are not soluble at a desired concentration including, but not limited to low nM or pM concentrations. In a non-limiting example, modifications of the gene encoding the protein, including, but not limited to the addition of other genetic sequences that facilitate protein solubility can be used to enhance the solubility properties of the lytic proteins.

In an alternative embodiment, the lytic proteins described in the disclosure may optionally be modified to adapt the DNA/protein sequence to the non-native system so that the protein may be produced in a non-native system. As a non-limiting example, the DNA sequence of the gene encoding a lytic protein that destroys methicillin-resistant *S. aureus* (MRSA) cells is not efficiently expressed in an *Escherichia coli*-based IVT system because *E. coli* has a preference for specific nucleotide triplets when producing proteins that are different from those preferred by *S. aureus*. By modifying the DNA sequence of the gene encoding a lytic protein for optimal expression in the *E. coli* IVT system, production of the lytic protein that is identical to that encoded by the *S. aureus* gene may be enhanced. Further, in an alternate embodiment, the lysin may be modified by manipulating the DNA sequence of the portion of the gene that encodes the C-terminal end of the lytic protein because this part of the protein provides target specificity to the enzyme, thereby producing a chimeric protein that attacks specific moieties of a bacterial cell wall in a different species of bacteria.

In an alternative embodiment, the lytic proteins described in the disclosure may include, but are not limited to one or more fragments comprising consecutive amino acid residues from at least 7 or more to less than all, at least 10 or more to less than all, at least 15 or more to less than all, preferably at least 20 or more to less than all, at least 25 or more to less than all, more preferably at least 35 or more to less than all, at least 40 or more to less than all, or at least 50 or more to less than all of amino acids constituting the lytic protein, or a variant thereof, and retains the one or more functional domains, or does not affect the functionality of the lytic protein.

In an alternative embodiment, the lytic proteins described in the disclosure may include, but are not limited to one or more variants comprising an amino acid sequence derived from the amino acid sequence of the lytic protein, or a fragment thereof, by the deletion, substitution, addition, or insertion of one or more amino acids, or to one or more variants that exhibit at least 50% identity or 60% similarity, preferably at least 70% to 90% identity or similarity, more preferably at least 90% identity or similarity, and more preferably at least 95% identity or similarity to the amino acid sequence of the lytic protein, or a fragment thereof.

Bacteria that can be targeted by the lysins of the invention may include numerous prokaryotic microbial species. The amide bond (CO—NH) targeted by amidases is located between N-acetylmuramic acid in the glycan chain and L-alanine in the cross-linking peptide subunit. The amide bond may be present in the peptidoglycan structure of both Gram-positive and Gram-negative bacteria from numerous species within various phyla, including, but not limited to Acidobacteria, Actinobacteria, Bacteroidetes, Chlamydiae, Cyanobacteria, Deinococcus-Thermus, Firmicutes, Fusobacteria, Nitrospira, Planctomycetes, Proteobacteria, and Spirochaetes. The phylum Proteobacteria includes, but is not limited to purple photosynthetic and non-photosynthetic gram-negative bacteria, including cocci, non-enteric rods and enteric rods, such as, for example, *Neisseria, Spirillum, Pasteurella, Brucella, Yersinia, Francisella, Haemophilus, Bordetella, Escherichia, Salmonella, Shigella, Klebsiella, Proteus, Pseudomonas, Bacteroides, Acetobacter, Aerobacter, Agrobacterium, Azotobacter, Spirilla, Serratia, Vibrio, Rhizobhium, Chlamydia, Rickettsia, Treponema* and *Fusobacterium*.

An alternative embodiment further relates to an isolated nucleic acid molecule encoding the polypeptide, fragment, variant, or derivative thereof or a fusion of the polypeptide, fragment, variant, or derivative. Non-limiting examples of isolated and/or purified nucleic acid molecules according to the present disclosure include a nucleic acid sequence according to SEQ ID NO: 1. One or more embodiments of the disclosure further relates to a recombinant vector comprising the nucleic acid molecule. The vector may provide for the constitutive or inducible expression of one or more polypeptides, fragments, variants, or derivatives thereof or a fusion of the polypeptide, fragment, variant, or derivative. One or more embodiments of the disclosure also relates to a method for obtaining one or more to polypeptides, fragments, variants derivatives or a fusion of the polypeptide, fragment, variant, or derivative from a microorganism, such as a genetically modified suitable host cell which expresses one or more polypeptides, fragments, variants, derivatives or a fusion of the polypeptide, fragment, variant, or derivative. The host cell may be a microorganism such as bacteria or yeast or an animal cell as e.g., a mammalian cell, e.g., a human cell. In one or more embodiments, the host cell is an *E. coli* cell. The host may be selected for biotechnological reasons, including, but not limited to yield, solubility, and costs and may also be selected for medical reasons, including, but not limited to a non-pathological bacteria or yeast or human cells. One or more embodiments of the disclosure further relates to a method for genetically transforming a suitable host cell in order to obtain the expression of the polypeptide, fragment, variant, or derivative thereof or fusion of the polypeptide, fragment, variant, or derivative, wherein the host cell is genetically modified by the introduction of a genetic material encoding one or more polypeptides, fragments, variants, or derivatives thereof or a fusion of the polypeptide, fragment, variant, or derivative into the host cell and obtain their translation and expression products.

The lysins described in this disclosure can be used to disrupt *Bacillus anthracis* cell walls, thus avoiding the use of the conventional methods for lysis of *Bacillus anthracis* cells, which do not provide consistent results essential for comparing genome copy numbers from cells grown with and without antibiotic. As a non-limiting example, conventional methods include, but are not limited to boiling, bead heating, and sonication.

In one or more embodiments, identification of a novel lysin protein may involve the review of whole genome databases for *Bacillus anthracis* and near neighbors; the selection of genes encoding potential lytic enzymes based on conserved amino acid motifs found in peptidoglycan hydrolases; the cloning of selected genes in an expression vector, the isolation of the proteins, and the testing for lytic activity against *Bacillus anthracis*. Candidates genes with highest activity as optionally determined by visible clearing or reduction of viable cells or by a decrease in the absorbance of a cellular suspension exposed to the lysin as recorded with a spectrophotometer, are selected, scaled up for production and purification, and optimized for lysis conditions. In one or embodiments, the preceding order is followed.

A novel lytic enzyme designated BQ22 was selected from five identified candidate genes: four from *Bacillus anthracis* and one from *Bacillus weihenstephanensis*. After cloning, enzymatic activity evaluation, protein solubility assessment, buffer optimization, lyophilization conditions of the candidate genes and gene products was performed, and stability studies were conducted.

The BQ22 lysin protein gene construct may comprise SEQ ID NO: 1 which optionally includes, but is not limited to a T7 promoter region (SEQ ID NO: 7), a His-Tag sequence (SEQ ID NO: 5), a lac operator (SEQ ID NO: 6), and a stop codon (see, for example, FIG. 9).

In one or more embodiments, the disclosure provides a newly characterized lytic enzyme BQ22 lysin. The BQ22 lysin and several engineered derivatives were expressed in *E. coli* and showed surprising stability after lyophilization as proven by their lytic activity after reconstitution. The new BQ22 lysin has excellent lytic activity against *Bacillus anthracis*.

In one or more embodiments, the new BQ22 lysin is an important component in a rapid antimicrobial susceptibility test developed for *Bacillus anthracis*. As shown in Table 1 below, conventional susceptibility testing of this species requires 16-20 hours of incubation time because the testing relies on visible growth for interpretation of the results. In one or more embodiments, conventional susceptibility testing includes, but is not limited to, broth microdilution, Etest, agar dilution, or disk diffusion. The novel lysins described in this disclosure, including, but not limited to the BQ22 lysin provides a mechanism/reagent necessary to ensure the consistent, reproducible cell lysis that is required to perform the rapid test in only 6 hours that uses real-time PCR to detect growth after an abbreviated incubation time.

TABLE 1

Time Required for Susceptibility Testing

| Agent* | Incubation for Isolation* | Incubation for conventional susceptibility testing | Incubation for rapid susceptibility testing |
| --- | --- | --- | --- |
| B. anthracis | 16 to 20 h | 16 to 20 h | 4 h |
| Y. pestis | 48 h | 24 to 48 h | 6 h |
| F. tularensis | 48 to 72 h | 48 h | 12 h |
| B. pseudomallei | 16 to 20 h | 16 to 20 h | 6 h |
| B. mallei | 16 to 20 h | 16 to 20 h | 6 h |

*A pure culture is required for susceptibility testing

The present disclosure provides various embodiments as described below. However, it should be noted that the present disclosure is not limited to the embodiments described herein.

A *Bacillus* lysin protein has been engineered and employed as a component of a rapid antimicrobial susceptibility assay, as shown in FIG. 1. FIG. 1 is a diagram showing a rapid antimicrobial susceptibility assay 100 according to one or more embodiments. In FIG. 1, the process begins at 105, by preparing a cell suspension with a concentration of approximately 5×10$^5$ cfu/ml. The suspension is then aliquoted into susceptibility testing plates at 110, a process that takes about 15 minutes. In one or more alternative embodiments, the cell suspension may comprise *Bacillus anthracis*. The inoculum is added to the plates which contain two-fold doubling dilutions of various antibiotics in the medium. These plates are then incubated at 115, at 35° C., for approximately 4 hours. The cells in the inoculated plate are then processed at 120 with BQ22 lysin for 15 minutes to release the DNA. Then, at 125, real-time PCR reactions are set up using the cell lysate produced by activity of BQ22, and the reaction mixtures are subjected to 45 cycles of amplification, which requires about 1.5 hours, after which the data are analyzed.

Figure 2:
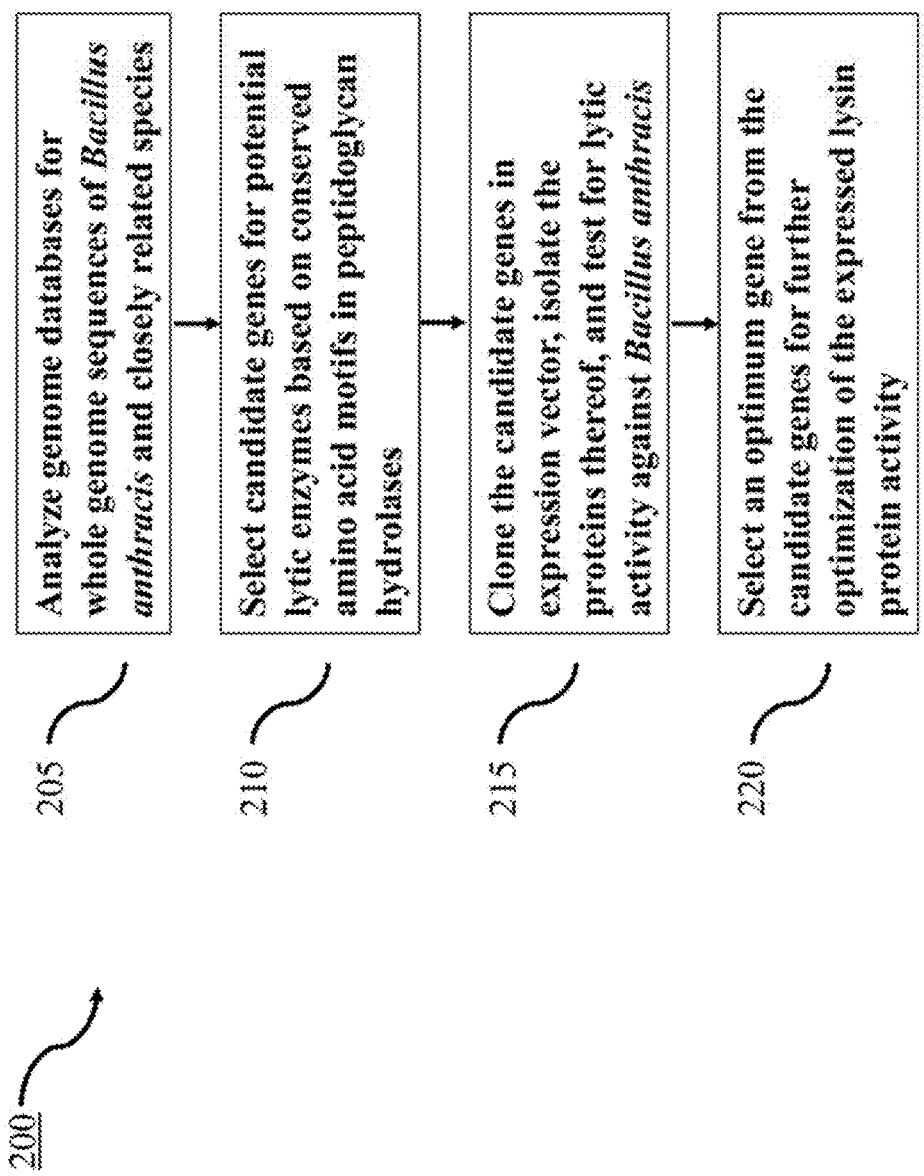
FIG. 2 is a flow diagram showing a method of finding and selecting a potential lysin agent for use in molecular diagnostic testing according to one or more embodiments.

FIG. 2 is a flow diagram showing a method of selecting a lysin agent for use in molecular diagnostic testing according to one or more embodiments of the present invention. As shown, the method 200 includes operation 205 where genome databases for *Bacillus anthracis* and near neighbors are analyzed. Next, the process continues to operation 210 where candidate genes encoding potential lytic enzymes are selected based on conserved amino acid motifs that are characteristic of peptidoglycan hydrolases.

From operation 210 the process continues to operation 215 where the candidate genes are cloned in an expression vector and proteins thereof are isolated and tested for lytic activity against *Bacillus anthracis*.

Next from operation 215, the process continues to operation 220 where an optimum gene of the candidate genes is selected for optimizing lysis conditions.

Approximately 140 novel lysin candidates were identified. Of the 140 candidates, 13 candidates (Tables 2 and 3 shown below) were cloned, sequenced, and tested for activity against *Bacillus anthracis*. A 96-well plate format assay was created to simultaneously test the activity of multiple lysin proteins against *Bacillus anthracis* under multiple conditions.

TABLE 2

Potential Candidate Lysin Proteins Examined In Vitro. (No Activity Observed)

| Protein | Organism | Accession No. | Predicted Function | Testing Conditions |
|---|---|---|---|---|
| BAH_A0050 | *Bacillus anthracis* str. A0442 | ZP_02395105 | Endopeptidase, Amidase | 50 mM phosphate, (pH 5.0, pH 6.0, pH 7.0, pH 8.0) @35° C., +/−0.1% Triton X-100; phosphate-buffered saline, (pH 7.4) @35° C., +/−0.1% Triton X-100; 50 mM Tris buffer, pH 6.5, pH 7.5, pH 8.5 @ 35° C., +/−0.1% Triton X-100; 50 mM Tris, 100 mM NaCl @ 35° C., +/−0.1% Triton X-100 |
| pE33L466_0234 | *Bacillus cereus* E33L | YP_245729.1 | Conserved hypothetical protein | 50 mM phosphate, (pH 5.0, pH 6.0, pH 7.0, pH 8.0) @35° C., +/−0.1% Triton X-100; phosphate-buffered saline, (pH 7.4) @35° C., +/−0.1% Triton X-100; 50 mM Tris buffer, pH 6.5, pH 7.5, pH 8.5 @ 35° C., +/−0.1% Triton X-100; 50 mM Tris, 100 mM NaCl @ 35° C., +/−0.1% Triton X-100 |
| BA_0796 | *Bacillus anthracis* str Ames | NP_843315.1 | Hypothetical protein | 50 mM phosphate, (pH 5.0, pH 6.0, pH 7.0, pH 8.0) @35° C., +/−0.1% Triton X-100; phosphate-buffered saline, (pH 7.4) @35° C., +/−0.1% Triton X-100; 50 mM Tris buffer, pH 6.5, pH 7.5, pH 8.5 @ 35° C., +/−0.1% Triton X-100; 50 mM Tris, 100 mM NaCl @ 35° C., +/−0.1% Triton X-100 |
| BA_5104 | *Bacillus anthracis* str. Ames | NP_847290.1 | D-Ala-D-Ala carboxypeptidase | 50 mM phosphate, (pH 5.0, pH 6.0, pH 7.0, pH 8.0) @35° C., +/−0.1% Triton X-100; phosphate-buffered saline, (pH 7.4) @35° C., +/−0.1% Triton X-100; 50 mM Tris buffer, pH 6.5, pH 7.5, pH 8.5 @ 35° C., +/−0.1% Triton X-100; 50 mM Tris, 100 mM NaCl @ 35° C., +/−0.1% Triton X-100 |
| BceRKBAB4_2909 | *Bacillus weihenstephanensis* KBAB4 | ABY44097.1 | amidase | 50 mM phosphate, (pH 5.0, pH 6.0, pH 7.0, pH 8.0) @35° C., +/−0.1% Triton X-100; phosphate-buffered saline, (pH 7.4) @35° C., +/−0.1% Triton X-100; 50 mM Tris buffer, pH 6.5, pH 7.5, pH 8.5 @ 35° C., +/−0.1% Triton X-100; 50 mM Tris, 100 mM NaCl @ 35° C., +/−0.1% Triton X-100 |
| BA_0224 | *Bacillus anthracis* str. Ames | AAP24267 | lysozyme-like LYZ domain | 50 mM phosphate (pH 6.0, pH 7.0, pH 8.0,) +/−0.1% Triton X-100, +/1 1 mM DTT, @28° C.; phosphate-buffered saline (PBS) pH 7.4, +/−0.1% Triton-X, +/−100 mM DTT, @28° C.; 50 mM Tris (pH 6.5, pH 7.5, pH 8.5), +/−1 mM DTT, @28° C.; 50 mM Tris (pH 7.5, pH 8.5), +/−0.1% Triton X-100, +/−1 mM metals @28° C.; 50 mM Tris (pH 7.5, pH 8.5) +/−100 mM NaCl, +/−1 mM DTT, +/−0.1% Triton X-100; 50 mM MES pH 5.2, +/−0.1% Triton X-100, +/−1 mM DTT, +/−1 mM metals @ 28° C.; 50 mM sodium acetate pH 5.2, +/−0.1% Triton X-100, +/−1 mM DTT, +/−1 mM metals, @ 28° C. |
| BA_3893 | *Bacillus anthracis* str. Ames | NP_846140 | Putative cell wall hydrolase | 50 mM phosphate (pH 6.0, pH 7.0, pH 8.0,) +/−0.1% Triton X-100, +/1 1 mM DTT, @28° C.; phosphate-buffered saline (PBS) pH 7.4, +/−0.1% Triton-X, +/−100 mM DTT, @28° C.; 50 mM Tris (pH 6.5, pH 7.5, pH 8.5), +/−1 mM DTT, @28° C.; 50 mM Tris (pH 7.5, pH 8.5), +/−0.1% Triton X-100, +/−1 mM metals @28° C.; 50 mM Tris (pH 7.5, pH 8.5) +/−100 mM NaCl, +/−1 mM DTT, +/−0.1% Triton X-100; 50 mM MES pH 5.2, +/−0.1% Triton X-100, +/−1 mM DTT, +/−1 mM metals @ 28° C.; 50 mM sodium acetate pH 5.2, +/−0.1% Triton X-100, +/−1 mM DTT, +/−1 mM metals, @ 28° C. |
| BA_3698 | *Bacillus anthracis* str. Ames | NP_845961 | amidase | 50 mM phosphate (pH 6.0, pH 7.0, pH 8.0,) +/−0.1% Triton X-100, +/1 1 mM DTT, @28° C.; phosphate-buffered saline (PBS) pH 7.4, |

TABLE 2-continued

Potential Candidate Lysin Proteins Examined In Vitro. (No Activity Observed)

| Protein | Organism | Accession No. | Predicted Function | Testing Conditions |
|---|---|---|---|---|
| BA_1818 | Bacillus anthracis str. Ames | NP_844239.1 | glucosaminidase | +/−0.1% Triton-X, +/−100 mM DTT, @28° C.; 50 mM Tris (pH 6.5, pH 7.5, pH 8.5), +/−1 mM DTT, @28° C.; 50 mM Tris (pH 7.5, pH 8.5), +/−0.1% Triton X-100, +/−1 mM metals @28° C.; 50 mM Tris (pH 7.5, pH 8.5) +/−100 mM NaCl, +/−1 mM DTT, +/−0.1% Triton X-100; 50 mM MES pH 5.2, +/−0.1% Triton X-100, +/−1 mM DTT, +/−1 mM metals @ 28° C.; 50 mM sodium acetate pH 5.2, +/−0.1% Triton X-100, +/−1 mM DTT, +/−1 mM metals, @ 28° C. 50 mM phosphate (pH 6.0, pH 7.0, pH 8.0,) +/−0.1% Triton X-100, +/1 1 mM DTT, @28° C.; phosphate-buffered saline (PBS) pH 7.4, +/−0.1% Triton-X, +/−100 mM DTT, @28° C.; 50 mM Tris (pH 6.5, pH 7.5, pH 8.5), +/−1 mM DTT, @28° C.; 50 mM Tris (pH 7.5, pH 8.5), +/−0.1% Triton X-100, +/−1 mM metals @28° C.; 50 mM Tris (pH 7.5, pH 8.5) +/−100 mM NaCl, +/−1 mM DTT, +/−0.1% Triton X-100; 50 mM MES pH 5.2, +/−0.1% Triton X-100, +/−1 mM DTT, +/−1 mM metals @ 28° C.; 50 mM sodium acetate pH 5.2, +/−0.1% Triton X-100, +/−1 mM DTT, +/−1 mM metals, @ 28° C. |

Three of the 13 novel lysin candidates, BceRK-BAB4_3364, BA_0898, and BA_2528, (Table 3 shown below) were found to hydrolyze *Bacillus anthracis* peptidoglycan, as demonstrated by a decrease in absorbance at A600 nm, with BA_2528 having the greatest activity when tested with crude lysates of *E. coli* expressing the lysin protein. BA_2528 is a predicted amidase of molecular mass (MM) ~43 kDa (FIGS. 3-4), that is shown herein to be active against vegetative cells of *Bacillus anthracis* Sterne (FIG. 5).

TABLE 3

Candidate Lysin Proteins Examined In Vitro Having Activity Against *Bacillus anthracis*.

| Protein ID | Organism | Accession No. | Predicted Function | Activity Notes | Expressed from Plasmid |
|---|---|---|---|---|---|
| BceR KBAB4_3364 | *Bacillus Weihenstephanensis* KBAB4 | YP_001646166.1 | muramidase | Maximum activity at 50 mM phosphate, pH 5.0 @ 35° C. Conditions tested: 50 mM phosphate (pH 5.0, pH, 6.0, pH 7.0, pH 8.0) @ 30° C. and @ 35° C.; +/−0.1% Triton X-100; 50 mM Tris (pH 6.5, pH 7.5, pH 8.5), +/−0.1% Triton X-100, +/−100 mM NaCl, @ 30° C. and 35° C. | pBQ11 |
| BA_0898 | *Bacillus anthracis* str. *Ames* | NP_843409 | amidase | Maximum activity at 50 mM Tris, pH8.5 w/0.1% Triton X-100. Conditions tested: 50 mM phosphate (pH 5.0, pH, 6.0, pH 7.0, pH 8.0) @ 30° C. and @35° C.;, +/−0.1% Triton X-100; 50 mM Tris (pH 6.5, pH 7.5, pH 8.5), +/−0.1% Triton X-100, +/−100 mM NaCl, @ 30° C. and 35° C. | pBQ15 |
| BA_2528* | *Bacillus anthracis* str. *Ames* | NP_844897 | amidase | Maximum activity at 50 mM Tris, pH 7.5-8.5. Conditions tested: 50 mM phosphate (pH 5.0, pH 6.0, pH 7.0, pH 8.0), +/−0.1% Triton X-100, @35° C.; phosphate-buffered saline (PBS), pH 7.4, +/−0.1% Triton X-100, @ 35° C.; 50 mM Tris (pH 6.5, pH 7.5, pH 8.5), +/−0.1% Triton X-100, +/−100 mM NaCl, @35° C.; 50 mM Tris (pH 8.5), +/−1 mM EDTA; 50 mM Tris (pH 7.5), 1% Trixton X-100, | pBQ13 pBQ22 pBQ23 |

TABLE 3-continued

Candidate Lysin Proteins Examined In Vitro Having Activity Against *Bacillus anthracis*.

| Protein ID | Organism | Accession No. | Predicted Function | Activity Notes | Expressed from Plasmid |
|---|---|---|---|---|---|
| | | | | 1 mM or 10 mM of one of the following (ZnCl$_2$, MnCl$_2$, CaCl$_2$, or MgCl$_2$). | |

Figure 3:
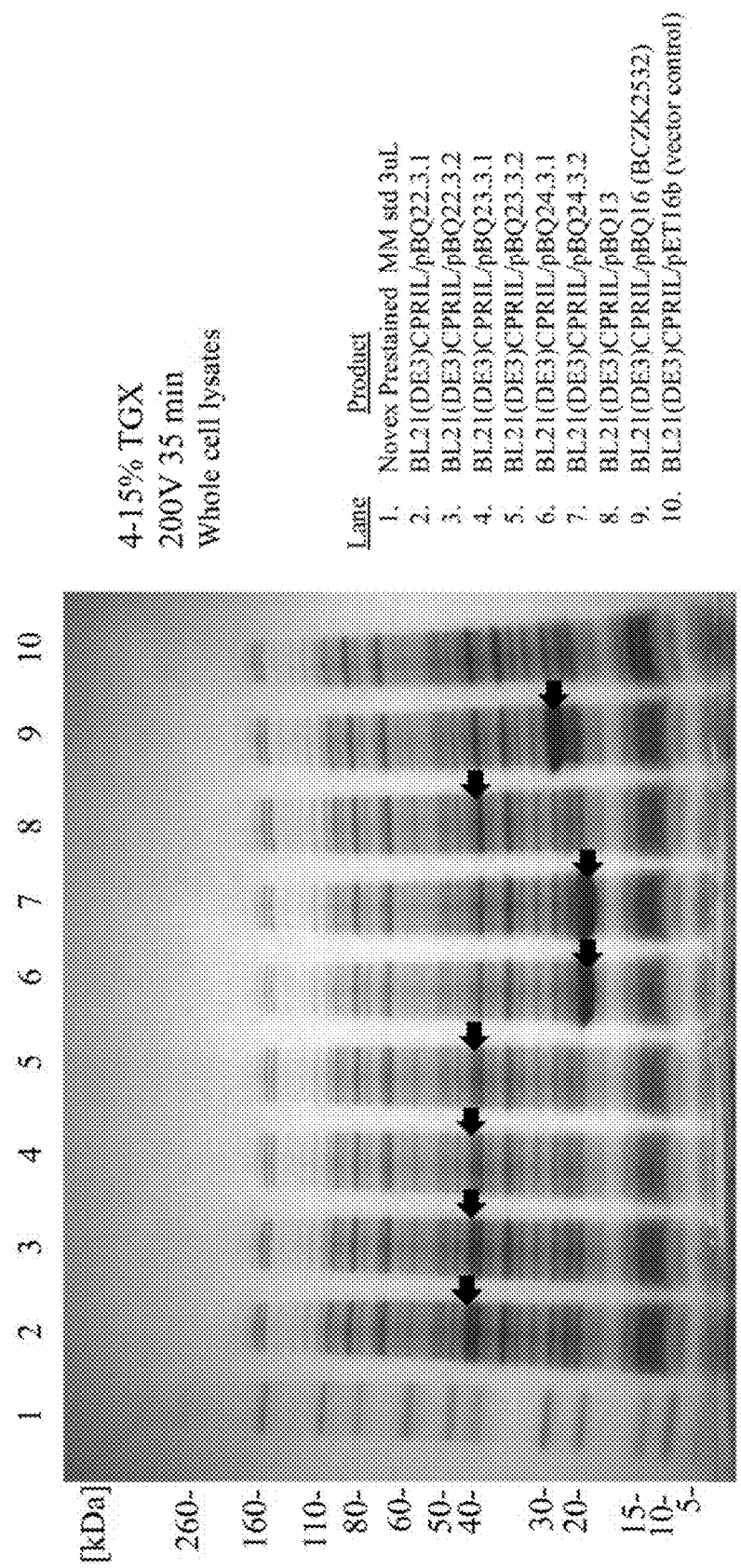
FIG. 3 illustrates a SDS-PAGE of proteins in whole cell lysates from IPTG-induced BL21 strains.

In FIG. 3, the arrows denote induction products for BQ22 (BA_2528 N-terminal 6×His) in lanes 1 and 2 (shown as pBQ22.3.1 and pBQ22.3.2 respectively), BQ23 (BA_2528 C-terminal 6×His) in lanes 3 and 4 (shown as pBQ23.3.1 and pBQ23.3.2 respectively), BQ24 (BA 2528 Catalytic domain only) in lanes 5 and 6 (shown as pBQ24.3.1 and pBQ24.3.2 respectively), BQ13 (BA_2528 wild type) in lane 8 (shown as pBQ13), and BQ16 (BCZK2532 wild type) in lane 9 (shown as pBQ16) with Molecular Mass markers in kiloDaltons (kDa) in lane 1 and pET16b vector control in lane 10 on a SDS-PAGE gradient gel.

Figure 4:
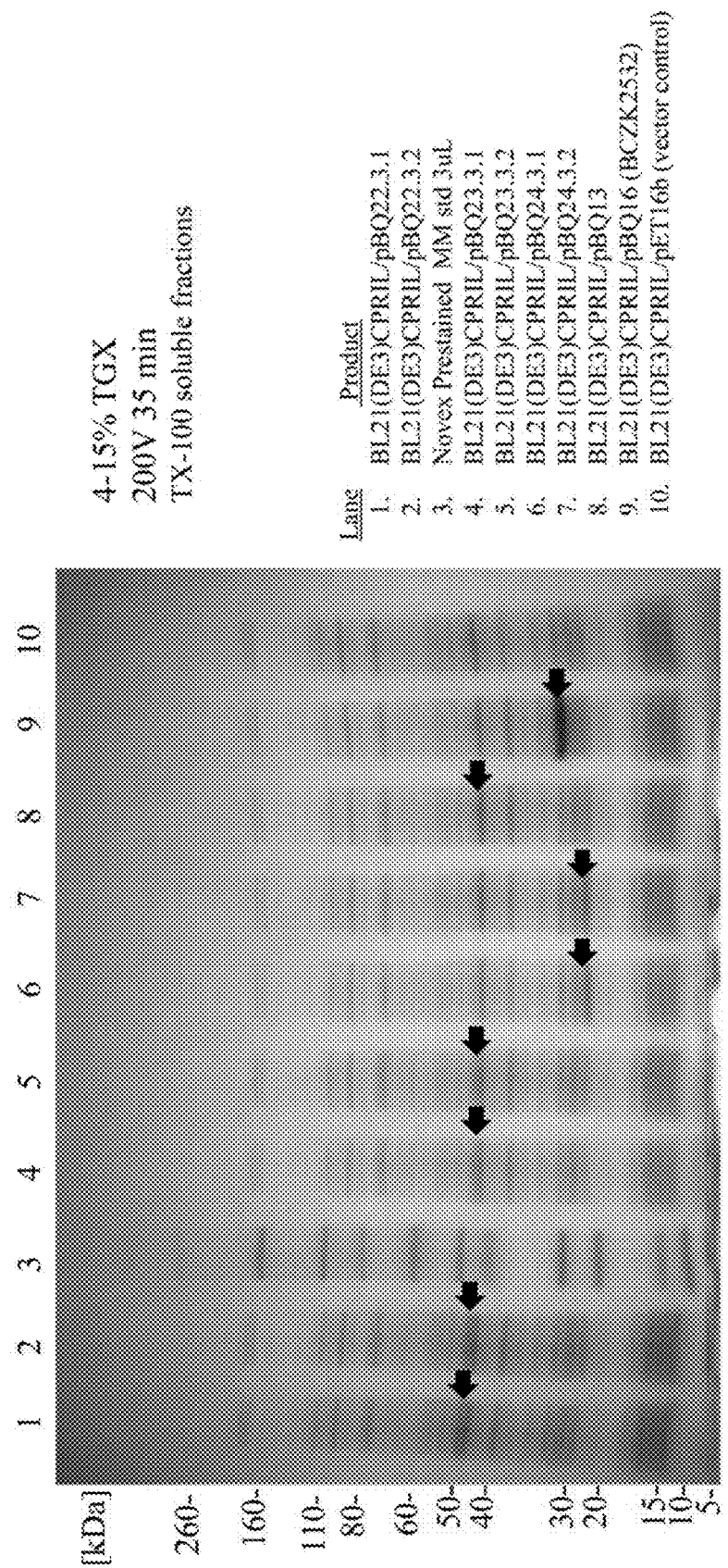
FIG. 4 illustrates a SDS-PAGE gradient gel of the Triton X-100 (Sigma Aldrich Co., St. Louis, Mo.) soluble protein fractions from IPTG-induced BL21 Strains.
Figure 5:
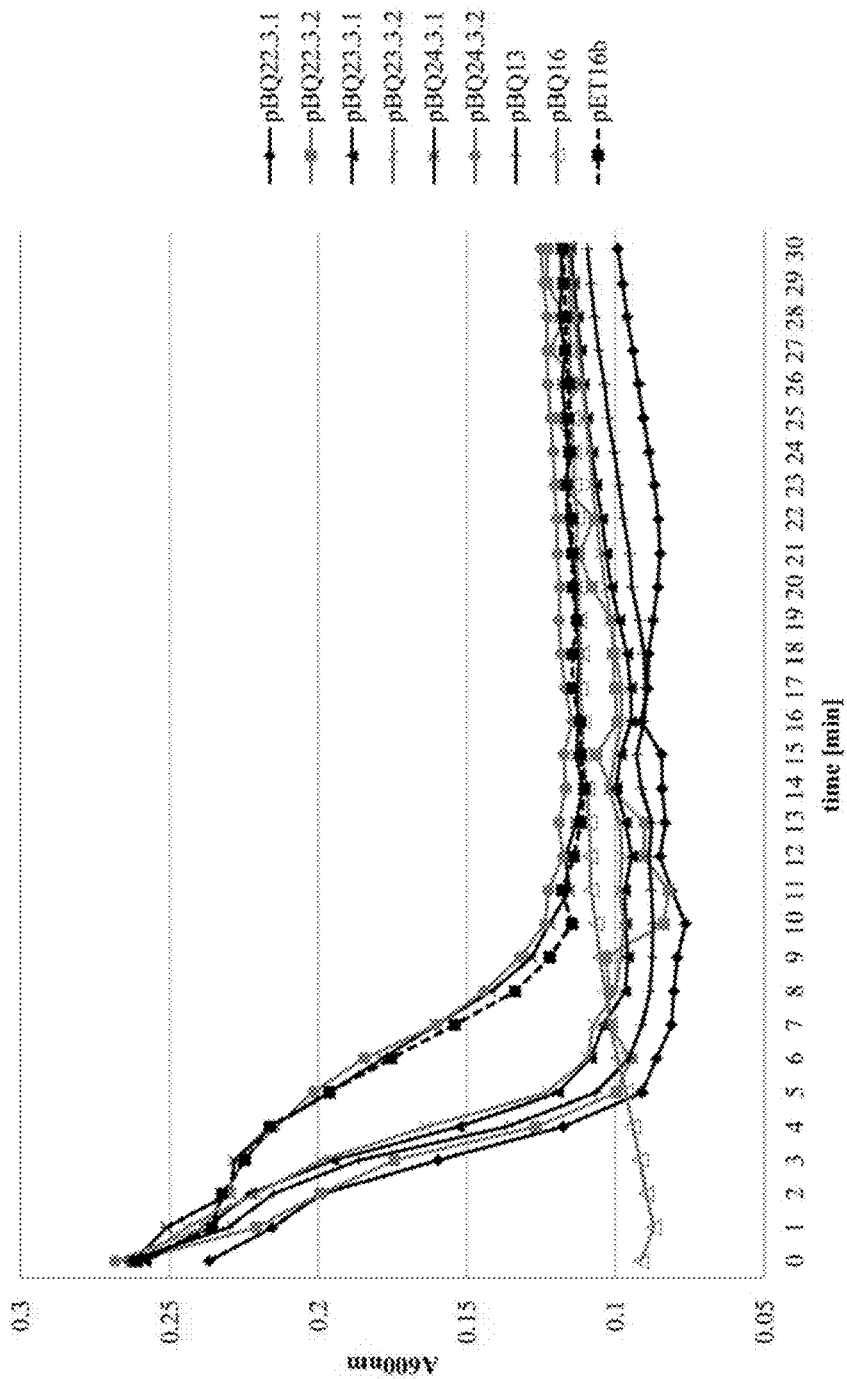
FIG. 5 is a graph illustrating lytic activity over a 30 min time period when *Bacillus anthracis* vegetative cells are exposed to crude *E. coli* lysates that contain the expressed lysin protein.

In FIG. 4, the arrows denote induction product for BQ22 (BA_2528 N-terminal 6×His) in lanes 1 and 2 (shown as pBQ22.3.1 and pBQ22.3.2 respectively), BQ23 (BA_2528 C-terminal 6×His) in lanes 4 and 5 (shown as pBQ23.3.1 and pBQ23.3.2 respectively), BQ24 (BA_2528 Catalytic domain only) in lanes 6 and 7 (shown as pBQ24.3.1 and pBQ24.3.2 respectively), BQ13 (BA 2528 wild type) in lane 8 (shown as pBQ13), and BQ16 (BCZK2532 wild type) in lane 9 (shown as pBQ16) with Molecular Mass markers in kiloDaltons (kDa) in lane 3 and pET16b vector control in lane 10 on a SDS-PAGE gradient gel.

FIG. 5 illustrates a graph showing lysin activity data from testing crude lysates of IPTG-induced *E. coli* that were incubated with vegetative cells of *Bacillus anthracis* Sterne at 35° C. over time at the buffer conditions indicted beside the graph. The decrease in A600 was monitored with a Spectramax 384 Plus Spectrophotometer. Samples tested were BQ13 (BA_2528 wild type) shown as pBQ13, BQ22 (BA_2528 N-terminal 6×HisTag) shown as pBQ22.3.1 and pBQ22.3.2, BQ23 (BA 2528 C-terminal 6×HisTag) shown as pBQ23.3.1 and pBQ23.3.2, BQ24 (BA_2528 Catalytic domain only, untagged) shown as pBQ24.3.1 and pBQ24.3.2, BQ16 (BCZK2532, positive control) shown as pBQ16, and pET16b (vector control) shown as pET16b. Addition of BCZK2532 caused all cells to lyse before recording could begin, and thus the curve appears as a flat line.

Figure 6:
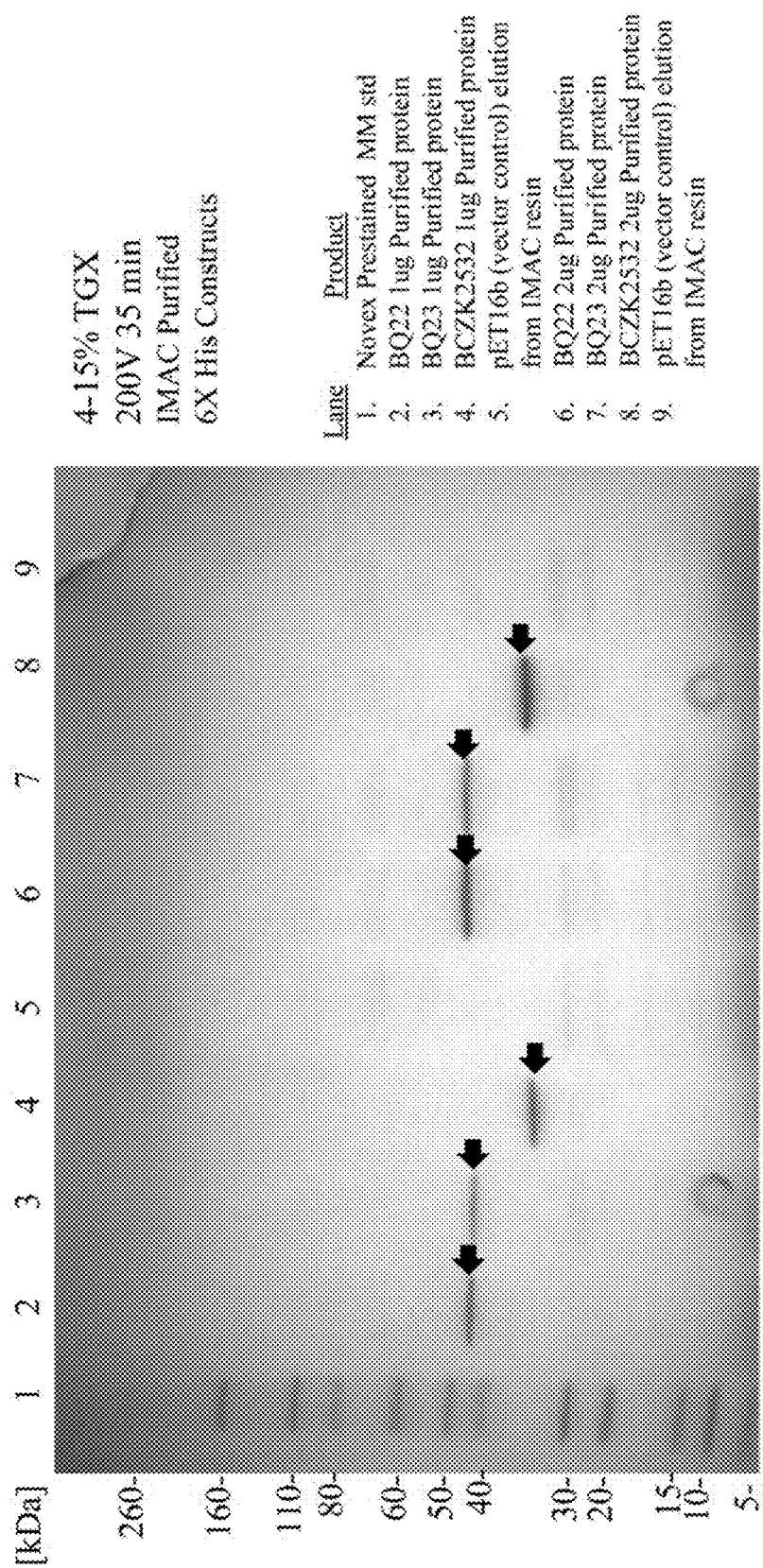
FIG. 6 illustrates a 4%-15% SDS-PAGE gradient gel stained to show IMAC-purified BQ22 (BA_2528 N-terminal 6×His), BQ23 proteins (BA_2528 C-terminal 6× His), and BCZK2532 fusion constructs.

FIG. 6 illustrates a comparison of 1 or 2 μg of Immobilized Metal Ion Affinity Chromatography (IMAC)-purified proteins on a 4-15% gradient SDS-PAGE gel, from the 6×HisTag constructs BQ22 (lanes 2 and 6), BQ23 (lanes 3 and 7), BCZK2532 (lanes 4 and 8), 1 μg from the pET16b vector control (lanes 5 and 9), respectively. Molecular mass markers are located in lane 1 on this gel. Lanes 2, 3, and 4 contained 1 μg protein and lanes 6, 7, and 8 contain 2 μg protein.

Figure 7:
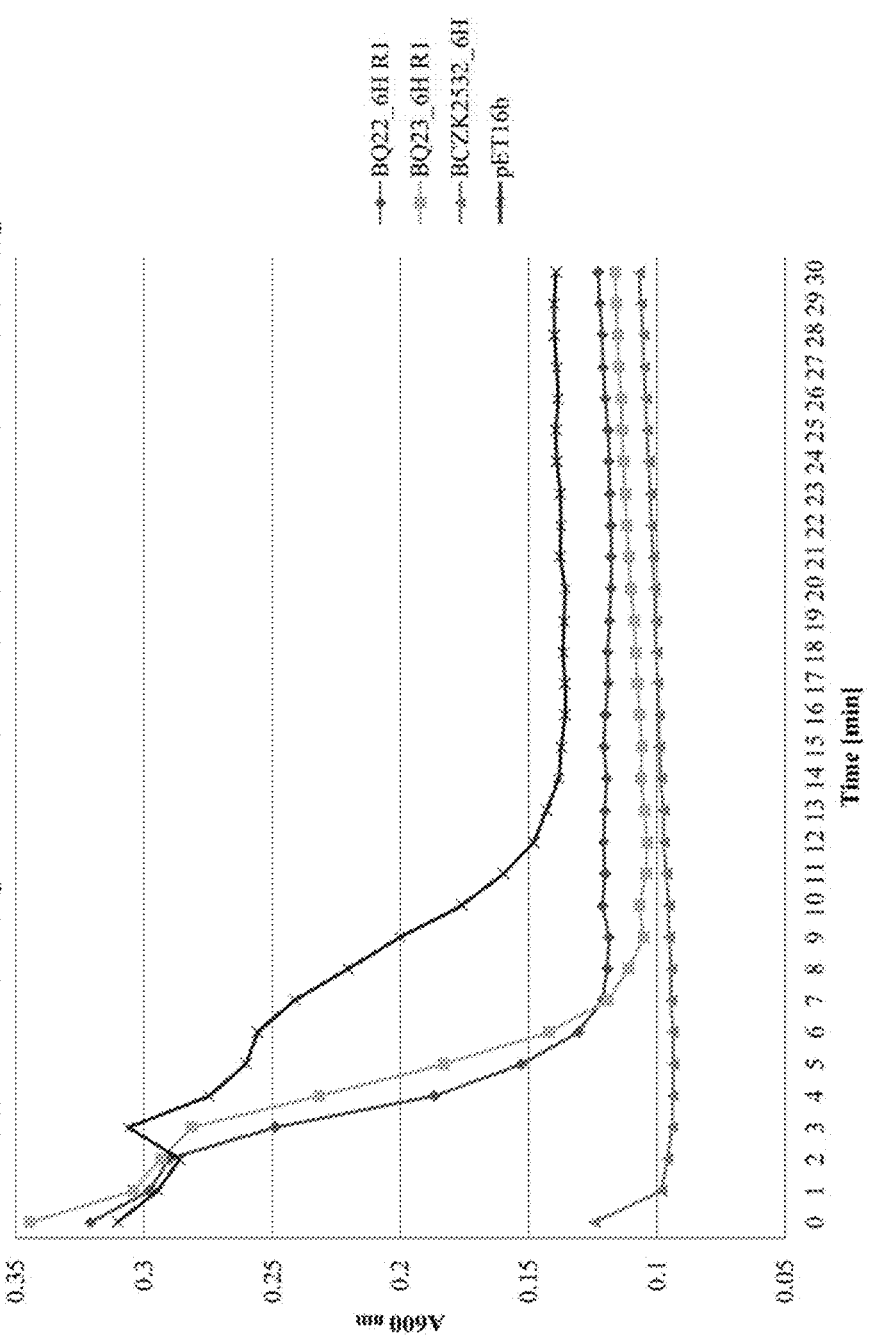

FIG. 7 illustrates enzyme activity for normalized molar amounts of purified BQ22 (BA 2528 N-terminal 6×H) shown as BQ22_6H R1, BQ23 (BA_2528 C-terminal 6×H) shown as BQ23_6H R1, and BCZK2532 shown as BCK2532_6H (positive control for purification and activity), and pET16b (vector control) shown as pET16b, added to exponential phase *Bacillus anthracis* Sterne in 50 mM Tris, pH 7.5, containing 0.1% Triton X-100 at 35° C. The decrease in absorbance at A600 nm was monitored with a Spectramax 384 Plus Spectrophotometer. R1 denotes the use of only one of the two replicates when plotting data. The addition of BCZK2532 caused all cells to lyse before recording could begin, and thus the curve appears as a flat line.

The IMAC purified BQ22 is also active against *Yersinia pestis*; see for example, FIG. 8, wherein 500 ng of IMAC-purified BQ22 was added to EDTA-treated *Yersinia pestis* cells at the conditions shown in Wash buffer (W, to remove EDTA) and Assay buffer (A), which were mixtures of Tris, pH 7.5 or pH 8.0, with 1% or 0.1% Triton X-100 with or without either 0.1% or 1.0% Triton X-100. Wash buffer (W) and assay buffer (A) were Tris, pH 7.5 or pH 8.0. The results illustrate a decrease in absorbance at A600 nm, as monitored by a Spectramax 384 Plus Spectrophotometer (Molecular Devices, LLC, Sunnyvale, Calif.).

The BCZK2532 protein is encoded on the *B. cereus* E33L genome, and the protein differs by only one conservative amino acid change from the same protein encoded by gamma phage on the *Bacillus anthracis* genome. *B. cereus* E33L is the closest known relative of *Bacillus anthracis*. The closest known relatives of *B. cereus* E33L are *Bacillus anthracis* and *B. thuringiensis* 97-27 as defined by an abundance of phylogenetic and genome sequencing criteria. In contrast. *B. thuringiensis* HD1 and HD560 are only distantly related to *B. cereus* E33L while *B. thuringiensis* HD658 is more closely related but not as closely related as the other two isolates. Non-limiting experiments described in this disclosure, including, but not limited to those related to percent survival as a function of relatedness, indicate that the more closely related an isolate is to the bacterial strain from which the lytic protein gene was derived, the more effective the lytic protein is in lysing cells of that isolate.

In a further aspect, the lysins can be used to target other Gram-negative bacteria such as *Yersinia pestis, Francisella tularensis, Burkholderia pseudomallei* and other Gram-negative bacilli and cocci. Non-limiting examples include, but are not limited to, *Hemophilus influenzae, Klebsiella pneumoniae, Legionella pneumophila, Pseudomonas aeruginosa, Escherichia coli, Proteus mirabilis, Enterobacer cloacae, Serratia marcescens, Helicobacter pylori, Salmonella enteritidis*, and *Salmonella typhi*. Polymyxins and other antibiotics that disrupt the structure of Gram-negative outer membranes can be used against Gram-negative bacteria, however, these antibiotics are relatively neurotoxic and nephrotoxic, so high concentrations may be contraindicated in some circumstances. In one or more embodiments, very low concentrations of these antibiotics in combination with the lytic proteins described in this disclosure, including, but not limited to BQ22 lysin are expected to result in rapid destruction of the Gram-negative pathogen. Low concentrations of polymyxins will increase the permeability of the Gram-negative outer membrane, facilitating exposure of the inner cell wall to the lytic proteins described in this disclosure, resulting in rapid cell lysis.

Additional embodiments include, but are not limited to, bacteria that can be effectively lysed with the lysins described in this disclosure include any bacterial species that contain the chemical bonds in peptidoglycan recognized by the four classes of lytic proteins. A review of some pathogenic bacteria genome sequences reveals that a significant number contains at least six to eight genes encoding the four classes of lytic proteins. Not all lytic proteins are expected to have the same effectiveness, so testing of the qualitative and quantitative lytic activity of a candidate lysin is required to determine relative activity, enzyme stability and other properties in order to identify the specific lytic enzyme that is the best choice for a particular use.

In other embodiments, the methods described herein can be performed to extract DNA from the new pathogen and subject the DNA to deep sequencing to provide an unfinished genome sequence using available DNA sequencing, sequence assembly and annotation technologies. In these methods, it is possible to identify genes encoding these enzymes, cloning, expression and purification of the lytic proteins and production of this material within a short period of time without need of identifying the pathogen.

In other embodiments, the lysins described in this disclosure can be used to decontaminate a surface or area or room or object contaminated with *Bacillus anthracis* and certain related bacteria by contacting the surface or area or room or object with one or more lysins described in this disclosure, such that the cell walls of *Bacillus anthracis* or certain related bacteria present on the surface or area or room or object will be lysed by the lysins described in this disclosure and the *Bacillus anthracis* or certain related bacteria effectively killed or neutralized. Examples of a surface or area or room or object that may be decontaminated by the lysins described in the disclosure may include, but are not limited to machines and instruments, building areas, furniture, articles of manufacture and personal effects, and foods. The lysins described in the disclosure may be used to decontaminate surfaces or areas or rooms or objects that humans contact with.

In other embodiments, the lysins described in this disclosure may be applied to the surface or area or room or object contaminated with *Bacillus anthracis* and certain related bacteria in a form that is suitable for the decontamination of a particular surface or area or room or object. As one non-limiting example, the lysins may be applied as a powder form to a particular surface or area or room or object and reconstituted with a fluid that allows the lysins to lyse the cell walls of *Bacillus anthracis* or certain related bacteria and effectively kill or neutralize them. As another non-limiting example, the lysins may be applied as a liquid form to a particular surface or area or room or object to lyse the cell walls of *Bacillus anthracis* or certain related bacteria and effectively kill or neutralize them.

In other embodiments, the lysins described in this disclosure can be used to disinfect a surface or area or room or object contaminated with at least *Bacillus anthracis* and certain related bacteria by contacting the surface or area or room or object with one or more lysins described in this disclosure, such that the cell walls of *Bacillus anthracis* or certain related bacteria present on the surface or area or room or object will be lysed by the lysins described in this disclosure and the *Bacillus anthracis* or certain related bacteria effectively killed or neutralized. Examples of a surface or area or room or object that may be disinfected by the lysins described in the disclosure may include, but are not limited to machines and instruments, building areas, furniture, articles of manufacture and personal effects, and foods. The lysins described in the disclosure may be used to disinfect surfaces or areas or rooms or objects that humans contact with.

In other embodiments, the lysins described in this disclosure may be applied to the surface or area or room or object contaminated with at least *Bacillus anthracis* and certain related bacteria in a form that is suitable for the disinfecting of a particular surface or area or room or object. As one non-limiting example, the lysins may be applied as a powder form to a particular surface or area or room or object and reconstituted with a fluid that allows the lysins to lyse the cell walls of *Bacillus anthracis* or certain related bacteria and effectively kill or neutralize them. As another non-limiting example, the lysins may be applied as a liquid form to a particular surface or area or room or object to lyse the cell walls of *Bacillus anthracis* or certain related bacteria and effectively kill or neutralize them.

EXAMPLES

In the examples below, pBQ13 encoding BQ13 (BA_2528_wild type), and derivatives pBQ22, encoding BQ22 (BA_2528 N-terminal 6xHisTag), pBQ23, encoding BQ23 (BA_2528 C-terminal 6xHisTag), and pBQ24 encoding BQ24 (BA_2528 Catalytic domain only, untagged), were expressed from pET16b in *E. coli* BL21(DE3) Codon Plus RIL to maximize the possibility of expression of soluble active enzyme.

IPTG-induced whole cell lysates were analyzed by SDS PAGE/Coomassie staining to visualize expression of a protein with the predicted molecular weight; see, for example, FIG. 3.

Triton X-100 (TX-100)-soluble fractions from the lysates were analyzed by SDS PAGE/Coomassie staining to visualize the presence of the lysin candidate in the crude lysate fraction that was analyzed for activity; see, for example, FIG. 4.

Lysins were assayed for activity by monitoring the decrease in A600 of *Bacillus anthracis* Sterne at 35° C. upon addition of TX-100 extracted crude *E. coli* lysates of IPTG induced cells expressing the lysin of interest using the 96-well plate format in 50 mM Tris 7.5 0.1% TX-100, which was previously shown to be optimal for BQ13; see for example, FIG. 5. The lysins were purified from Triton X-100-extracted *E. coli* lysates using IMAC; see for example FIG. 6.

Normalized molar amounts (from 2.32E-2 nmol to 7.25E-4 nmol) of purified lysins were tested for activity against *Bacillus anthracis* Sterne and both BQ22 (BA_2528 N-terminal 6xH), and BQ23 (BA_2528 C-terminal 6xH) were active; see for example FIG. 7). Data from the addition of 2.32E-2 nmol purified protein is shown in FIG. 7.

Example I

Example Bacterial Strains and Growth Conditions:

*Escherichia coli* (*E. coli*) strains are cultured in Luria-Bertani broth (LB, Difco) at 28° C. Strain BL21(DE3) Codon Plus RIL (Stratagene), which lacks the outer membrane proteases Lon and OmpT, and which has a plasmid that encodes rare tRNAs for codons present in AT—rich organisms (such as *Bacillus anthracis*), was chosen for expression of lysin proteins. Ampicillin (Amp) is used at a concentration of 100 µg/mL in plates and at 125 µg/mL in liquid medium. Chloramphenicol (Cam) was used at 34 µg/mL in plates and liquid medium. The concentration of chloramphenicol was increased to 50 µg/mL in overnight cultures.

Example II

DNA Isolation and Manipulation:

Candidate lysin genes are amplified by PCR from strain specific genomic DNA using candidate lysin (CL)-specific primers that contain restriction sites compatible with the multi-cloning site of pET16b. PCR products are purified using a Qiagen PCR purification kit (Qiagen, Inc., Hilden, Germany) according to the manufacturer's instructions, and the concentration of the amplified DNA is determined using a Nanodrop 1000 spectrophotometer (X-Rite, Grand Rapids, Mich.). DNA fragments encoding the genes of interest are ligated into the pET16b(+) vector (Novagen), placing the candidate lysin sequence under the transcriptional control of the T7 promoter and under the translational control of the pET16b(+) strong RBS. Plasmid pET16b was chosen for expression of lysin proteins because it encodes lacI for high level repression of transcription prior to induction with IPTG. Ligation mixtures are transformed to *E. coli* XL10 Gold (Stratagene) according to the manufacturer's instructions and transformants are selected on LB/amp plates. Transformants are sub-cultured for purity on to LB/amp plates and plasmid isolations are prepared using a Qiagen miniprep spin kit according to the manufacturer's instructions. Plasmid DNA concentration is determined using a Nanodrop 1000 spectrophotometer. CL genes that are difficult to amplify directly from genomic DNA are TOPO cloned or re-amplified from initial PCR products and then cloned into pET16b using the appropriate restriction endonucleases.

Example III

DNA Sequencing:

Primers T7PSense having SEQ ID NO: 3 (5' cgatcccgcgaaattaatacgactcactatagg 3') and T7Tanti having SEQ ID NO: 4 (5' gctagttattgctcagcggtggc 3') are used to amplify the DNA encoding each CL from pET16b-based plasmids. PCR reactions are treated with ExoSAP-IT (Affymetrix) according to the manufacturer's instructions and quantified on a 0.8% agarose minigel (Invitrogen, Thermo Fisher Scientific., Inc, Waltham, Mass.) by estimation relative to a known amount of the NEB 1 Kb ladder (NEB). A series of CL-specific primers that provide at least 2x sequence coverage across the sequence are used with a BigDye chain terminator cycle sequencing kit (ABI) according to the manufacturer's instructions. An ABI 3130 XL automated DNA sequencer with analysis software v5.0 is used to generate sequence data. Sequencher (Gene codes) is used to assemble sequence data. BLASTn is used to verify correct sequence relative to the CL specific plasmid map. Candidates with confirmed correct sequences are transformed into *E. coli* BL21 (DE3) Codon plus RIL for protein expression.

Example IV

Expression of Candidate Lysins:

Strain BL BL21(DE3) Codon Plus RIL containing the plasmid of interest is incubated overnight at 28° C. in LB/Amp/Cam without shaking. The culture is then diluted 1:500 in fresh LB with Amp and Cam and cultured at 28° C. with shaking at 120 rpm until reaching A600 nm=0.4-0.6.

IPTG is added to a final concentration of 1 mM, and cells are cultured for a further 3 h. Cells are pelleted by centrifugation, the supernatant is removed, and the cell pellets flash frozen on dry ice. Cell pellets are stored at −80° C. until used in SDS PAGE or activity assays. The induction procedure may be modified based upon the observed characteristics of any CL when performing the initial induction as described.

Example V

SDS-PAGE: IPTG-induced cell pellets are resuspended in 1×SDS sample buffer and heated to 99° C. for 10 min in a heat block. Samples are analyzed by SDS-PAGE using a Bio-Rad 4-12% TGX minigel gel (Bio-Rad, Hercules, Calif.) at 200V for 35 min in Tris-glycine SDS running buffer. Gels are then stained with Simply Blue safe stain (Invitrogen) according to the manufacturer's instructions. The apparent molecular mass of protein products from IPTG induction experiments is determined by comparison to the Novex Sharp Prestained molecular mass standard (Invitrogen).

Example VI

Activity Assay:

All operations involving wildtype *Bacillus anthracis* are performed within a class IIA2 BSC in a select agent-registered laboratory using BSL-3 procedures. *Bacillus anthracis* Sterne, an avirulent select agent-excluded strain, is grown on LB plates at 35° C. overnight. After approximately 16 h growth, the cells are suspended in cation-adjusted Mueller Hinton broth with TES (CAMHB, Difco) to an absorbance of 0.1 using a Dade-Behring spectrophotometer, diluted 1:100 in LB and incubated for 4 h at 35° C., shaking at 120 rpm in a plastic flask with 0.22 µm aerator top. Cells are then captured on a 0.22 µm CA membrane using a vacuum apparatus, washed with d-H20 (Cellgro, Manassas, Va.), resuspended in d-H20 by vigorous vortexing and held at room temperature until used in the activity assay. All operations for preparation of *E. coli* lysates are performed at 4° C. unless otherwise noted. An IPTG-induced *E. coli* cell pellet is thawed, re-suspended in lysis buffer (25 mM Tris 8.0), and sonicated using a Covaris S220 adaptive focused acoustic sonicator. A fraction of the lysate is brought to a final concentration of 1% TX-100 and incubated 15 min. Lysates are centrifuged at 13,000 rpm for 2 min, the supernatant is transferred to new 1.5 mL Eppendorf tube, and a sample is removed for analysis of induction by SDS PAGE. An aliquot of 155 µL of *Bacillus anthracis* Sterne in d-H20 is added to a well of a 96-well plate containing 20 µL of 10× buffer such that, after adding 25 mL of crude cell lysate, the final concentration of 50 mM buffer is present in a 200 µL assay volume. Activity is analyzed under the following conditions, all of which may not be tested at any one given time: 50 mM acetate pH 5.2, 50 mM MES pH 5.2, 50 mM phosphate pH 6.0, 7.0, and 8.0, PBS pH 7.4, 50 mM Tris pH 6.5, 7.5, and 8.5. Any of the given reaction conditions can be modified by addition of NaCl, divalent cations, DTT, EDTA and Triton X-100 taking into consideration factors such as the solubility constants of the individual buffers when combined to the cation used; the effects of EDTA on the total concentration of metal ions such as $Zn^{2+}$; and the requirements of cofactors for enzymatic activity in some but not all lysin proteins. The temperature may also be varied. A 25 µL volume of crude lysate or purified protein at a predetermined concentration is added to initiate the reaction and bring the final volume to 200 µL. Plates are covered and incubated for 30 min in a Spectramax 384 plus (Molecular Devices) with A600 readings taken at 1 min intervals. Positive and negative controls are included; the positive control is IMAC-purified BCZK2532, and the negative control is re-suspension buffer.

Example VII

Purification of 6×HisTag Proteins:

All operations are performed at 4° C. unless otherwise specified. An IPTG-induced *E. coli* cell pellet is thawed at 4° C., resuspended in lysis buffer (25 mM Tris 8.0, 300 mM NaCl) and sonicated using a Covaris S220 adaptive focused acoustics sonicator. In the event that activity is detected in the TX-100 soluble fraction of the crude lysate activity assay as described above, Triton X-100 is added to a final concentration of 1% and the cell lysate is extracted for 30 min. Lysates are centrifuged at 4000 rpm for 10 min. The supernatant is transferred to a new tube containing HisPur Ni-NTA Resin (Thermo), and binding is conducted for 30 min. The Ni-NTA resin is washed, and the protein of interest is eluted from the resin according to the manufacturer's instructions.

The contents of all references cited in the present specifications and all cited references in each of those references are incorporated in their entirety by reference herein.

While many embodiments have been disclosed above, many other embodiments and variations are possible within the scope of the present disclosure as recognized by one of ordinary skill in the art and in the appended claims that follow. Accordingly, the details of the embodiments and examples provided are not to be construed as limiting. It is to be understood that the terms used herein are merely descriptive rather than limiting and that various changes and numerous equivalents may be made without departing from the spirit or scope of the claimed invention.

---

What is claimed:

1. A recombinant nucleic acid comprising a nucleotide sequence encoding a polypeptide comprising the amino acid sequence of SEQ. ID NO: 2, or fusion thereof.

2. The recombinant nucleic acid of claim 1, wherein the nucleotide sequence is operably linked to one or more control sequences.

3. The recombinant nucleic acid of claim 2, wherein the one or more control sequences is selected from a group consisting of: a promoter, a transcriptional start signal, a transcriptional stop signal, a translational start signal, and a translational stop signal.

4. The recombinant nucleic acid of claim 1, wherein the nucleotide sequence comprises SEQ ID NO: 1.

5. A vector comprising a recombinant nucleic acid comprising a nucleotide sequence encoding a polypeptide comprising the amino acid sequence of SEQ ID NO: 2, or a fusion thereof.

6. The vector of claim 5, wherein the nucleotide sequence is operably linked to one or more control sequences.

7. The vector of claim 6, wherein the one or more control sequences is selected from a group consisting of: a promoter, a transcriptional start signal, a transcriptional stop signal, a translational start signal, and a translational stop signal.

8. The vector of claim 5, wherein the nucleotide sequence comprises SEQ ID NO: 1.

9. A host cell transformed with a vector comprising a recombinant nucleic acid comprising a nucleotide sequence encoding a polypeptide comprising the am no acid sequence of SEQ ID NO: 2, or a fusion thereof.

10. The host cell of claim 9, wherein the nucleotide sequence is operably linked to one or more control sequences.

11. The host cell of claim 10, wherein the one or more control sequences is selected from a group consisting of: a promoter, a transcriptional start signal, a transcriptional stop signal, a translational start signal, and a translational stop signal.

12. The host cell of claim 9, wherein the nucleotide sequence comprises SEQ ID NO: 1.

13. An isolated polypeptide comprising the amino acid sequence of SEQ ID NO: 2, or a fusion thereof, the polypeptide having peptidoglycan hydrolase activity.

14. A method for producing a polypeptide with peptidoglycan hydrolase activity, comprising:
    (a) providing a host cell comprising a vector comprising a nucleotide sequence encoding the polypeptide with peptidoglycan hydrolase activity, wherein the nucleotide sequence is operably linked to one or more control sequences; and
    (b) culturing the host cell under culturing conditions; and
    (c) isolating the polypeptide,
    wherein the polypeptide comprises the amino acid sequence of SEQ ID NO: 2.

15. The method of claim 14, wherein the one or more control sequences is selected from a group consisting of: a promoter, a transcriptional start signal, a transcriptional stop signal, a translational start signal, and a translational stop signal.

16. The method of claim 14, wherein the nucleotide sequence comprises SEQ ID NO: 1.

17. A method for diagnosing the presence or absence of bacteria in a sample comprising:
    (a) providing a sample of the bacteria; and
    (b) incubating the sample of the bacteria in the presence of an isolated polypeptide comprising the amino acid sequence of SEQ ID NO: 2, or a fusion thereof, the polypeptide having peptidoglycan hydrolase activity, and
    (c) contacting the sample and the isolated polypeptide having peptidoglycan hydrolase activity with at least a first and a second oligonucleotide primer under conditions sufficient to provide polymerase-based nucleic acid amplification; and
    (d) detecting the presence or absence of an amplification product.

18. The method of claim 17, wherein the bacteria is a gram-positive bacteria.

19. The method of claim 18, wherein the gram-positive bacteria is a *Bacillus* species.

20. The method of claim 19, wherein the *Bacillus* species is *Bacillus anthracis*.

21. The method of claim 17, wherein the bacteria is a gram-negative bacteria.

22. The method of claim 21, wherein the gram-negative bacteria is a *Yersinia* species.

23. The method of claim 22, wherein the *Yersinia* species is *Yersinia pestis*.

24. The method of claim 17, wherein the polymerase-based nucleic acid amplification is quantitative polymerase chain reaction (QPCR).

25. A method for lysing bacteria comprising:
    (a) providing a sample of the bacteria; and
    (b) preparing an isolated polypeptide comprising the amino acid sequence of SEQ ID NO: 2, or a fusion thereof, the polypeptide having peptidoglycan hydrolase activity; and
    (c) incubating the isolated polypeptide with the bacteria.

26. The method of claim 25, wherein the bacteria is a gram-positive bacteria.

27. The method of claim 26, wherein the gram-positive bacteria is a *Bacillus* species.

28. The method of claim 27, wherein the *Bacillus* species is *Bacillus anthracis*.

29. The method of claim 25, wherein the bacteria is a gram-negative bacteria.

30. The method of claim 29, wherein the gram-negative bacteria is a *Yersinia* species.

31. The method of claim 30, wherein the *Yersinia* species is *Yersinia pestis*.

* * * * *

SEQUENCE LISTING

```
<160> NUMBER OF SEQ ID NOS: 7

<210> SEQ ID NO 1
<211> LENGTH: 1454
<212> TYPE: DNA
<213> ORGANISM: artificial
<220> FEATURE:
<223> OTHER INFORMATION: BQ22 lysin protein gene construct

<400> SEQUENCE: 1
cggtgatgcc ggccacgatg cgtccggcgt agaggatcga gatctcgatc ccgcgaaatt      60
aatacgactc actatagggg aattgtgagc ggataacaat tcccctctag aaataatttt     120
gtttaacttt aagaaggaga tataccatgg gccatcatca tcatcatcat agcgcagata     180
ctcacagatt cccagatgtt cctgcatggg ctgacaaatc cgttacttat ttagttgata     240
aacaagtatt gagtggttat ccagatggga cttttggttc aagtgataca ctagatagag     300
cttctgcagc aacaattatg actaaggctc ttggtataca cattgattta aatgcaaaac     360
catcttttaa agattcacaa aaccactggg gaacccctta tattgccgca gctgaaaagg     420
caggaatcat taaaggtgaa ggaaatggaa tatttaatcc ttctggaaaa gttactcgtg     480
ctgctatggc tactatgcta gtgaatgcat ataaactaca aaataaaaac actagcaatg     540
gacaaagtaa atttgaagat ttaaagggcc attggggtga aagttcgca aatactttaa      600 ttgatttgaa aatttcagtt ggtacagata tggctggca accaaataaa ttcataacac      660
gcgctgaagc tgcacaacta actgcaaaaa cagatatgct tcaatatagt catagtaatc     720
ctttagaaaa taaaaccata attattgatc ccggacatgg tggcgaagat cctggaaaag     780
acacaaaggg attacctgaa agtaagattg tactagacac ttctttacgt ctacaaaaat     840
tgcttgaaaa acatacacca tttacagttt tactaactcg taaatctgat actagaccag     900
gacatgatca aaaaagctct ttacaggaac gtgtgaaatt tgctaaacaa aatcaggggg     960
atatctttat aagtgttcat gcaaatgctt ttaatggtaa tgcaaaaggg acggaaacat    1020
actactataa atcttctaaa tctgaaaaaa caaatcctca tgtggaagag agtcgtgttt    1080
tagctgaaaa aattcaaact cgattagtag acgctcttca aacacgtgat agaggcgtta    1140
aacatggaga tcttcatgtt ataagagaaa atgacatgcc agctgtgtta acggaacttg    1200 ctttttataga taatggtatc gattacagta agttatctac agaaaacgga aggcagattg    1260
ctgcagaagc catttatgag gggatttag attattatga atggaaagga aataatgtat    1320
```

-continued

```
ctgaatatag gctgtaactc gaggatccgg ctgctaacaa agcccgaaag gaagctgagt    1380
tggctgctgc caccgctgag caataactag cataacccct tggggcctct aaacgggtct    1440
tgagggtttt tttg                                                       1454
```

<210> SEQ ID NO 2
<211> LENGTH: 396
<212> TYPE: PRT
<213> ORGANISM: artificial
<220> FEATURE:
<223> OTHER INFORMATION: BQ22 lysin protein

<400> SEQUENCE: 2

```
Met Gly His His His His His His Ser Ala Asp Thr His Arg Phe Pro
1               5                   10                  15

Asp Val Pro Ala Trp Ala Asp Lys Ser Val Thr Tyr Leu Val Asp Lys
            20                  25                  30

Gln Val Leu Ser Gly Tyr Pro Asp Gly Thr Phe Gly Ser Ser Asp Thr
        35                  40                  45

Leu Asp Arg Ala Ser Ala Ala Thr Ile Met Thr Lys Ala Leu Gly Ile
    50                  55                  60

His Ile Asp Leu Asn Ala Lys Pro Ser Phe Lys Asp Ser Gln Asn His
65                  70                  75                  80

Trp Gly Thr Pro Tyr Ile Ala Ala Ala Glu Lys Ala Gly Ile Ile Lys
                85                  90                  95

Gly Glu Gly Asn Gly Ile Phe Asn Pro Ser Gly Lys Val Thr Arg Ala
            100                 105                 110

Ala Met Ala Thr Met Leu Val Asn Ala Tyr Lys Leu Gln Asn Lys Asn
        115                 120                 125

Thr Ser Asn Gly Gln Ser Lys Phe Glu Asp Leu Lys Gly His Trp Gly
    130                 135                 140

Glu Lys Phe Ala Asn Thr Leu Ile Asp Leu Lys Ile Ser Val Gly Thr
145                 150                 155                 160

Asp Asn Gly Trp Gln Pro Asn Lys Phe Ile Thr Arg Ala Glu Ala Ala
                165                 170                 175

Gln Leu Thr Ala Lys Thr Asp Met Leu Gln Tyr Ser His Ser Asn Pro
            180                 185                 190

Leu Glu Asn Lys Thr Ile Ile Ile Asp Pro Gly His Gly Gly Glu Asp
        195                 200                 205

Pro Gly Lys Asp Thr Lys Gly Leu Pro Glu Ser Lys Ile Val Leu Asp
    210                 215                 220

Thr Ser Leu Arg Leu Gln Lys Leu Leu Glu Lys His Thr Pro Phe Thr
225                 230                 235                 240

Val Leu Leu Thr Arg Lys Ser Asp Thr Arg Pro Gly His Asp Gln Lys
                245                 250                 255

Ser Ser Leu Gln Glu Arg Val Lys Phe Ala Lys Gln Asn Gln Gly Asp
            260                 265                 270

Ile Phe Ile Ser Val His Ala Asn Ala Phe Asn Gly Asn Ala Lys Gly
        275                 280                 285

Thr Glu Thr Tyr Tyr Lys Ser Ser Lys Ser Glu Lys Thr Asn Pro
    290                 295                 300

His Val Glu Glu Ser Arg Val Leu Ala Glu Lys Ile Gln Thr Arg Leu
305                 310                 315                 320

Val Asp Ala Leu Gln Thr Arg Asp Arg Gly Val Lys His Gly Asp Leu
                325                 330                 335
```

```
His Val Ile Arg Glu Asn Asp Met Pro Ala Val Leu Thr Glu Leu Ala
        340                 345                 350

Phe Ile Asp Asn Gly Ile Asp Tyr Ser Lys Leu Ser Thr Glu Asn Gly
        355                 360                 365

Arg Gln Ile Ala Ala Glu Ala Ile Tyr Glu Gly Ile Leu Asp Tyr Tyr
        370                 375                 380

Glu Trp Lys Gly Asn Asn Val Ser Glu Tyr Arg Leu
385                 390                 395

<210> SEQ ID NO 3
<211> LENGTH: 33
<212> TYPE: DNA
<213> ORGANISM: artificial
<220> FEATURE:
<223> OTHER INFORMATION: Synthetic primer - T7PSense

<400> SEQUENCE: 3
cgatcccgcg aaattaatac gactcactat agg                           33

<210> SEQ ID NO 4
<211> LENGTH: 23
<212> TYPE: DNA
<213> ORGANISM: artificial
<220> FEATURE:
<223> OTHER INFORMATION: Synthetic primer - T7Tanti

<400> SEQUENCE: 4
gctagttatt gctcagcggt ggc                                      23

<210> SEQ ID NO 5
<211> LENGTH: 18
<212> TYPE: DNA
<213> ORGANISM: artificial
<220> FEATURE:
<223> OTHER INFORMATION: His-Tag sequence

<400> SEQUENCE: 5
catcatcatc atcatcat                                            18

<210> SEQ ID NO 6
<211> LENGTH: 24
<212> TYPE: DNA
<213> ORGANISM: artificial
<220> FEATURE:
<223> OTHER INFORMATION: Lac operator

<400> SEQUENCE: 6
gggaattgtg agcggataac aatt                                     24

<210> SEQ ID NO 7
<211> LENGTH: 20
<212> TYPE: DNA
<213> ORGANISM: artificial
<220> FEATURE:
<223> OTHER INFORMATION: T7 promoter

<400> SEQUENCE: 7
taatacgact cactataggg                                          20
```